US011712361B2

(12) United States Patent
Pepper et al.

(10) Patent No.: US 11,712,361 B2
(45) Date of Patent: *Aug. 1, 2023

(54) NASAL DILATOR DEVICES

(71) Applicant: ASAP Breatheassist Pty Ltd, Armadale (AU)

(72) Inventors: Elizabeth Jane Pepper, Brunswick (AU); Michael Ralph Burgess Johnson, Hawthorn (AU); Justin Robert Armistead, The Basin (AU); Toby James Hartley, Ferntree Gully (AU); George Kotsiopoulos, Edithvale (AU)

(73) Assignee: ASAP Breatheassist Pty Ltd, Cremorne (AU)

( * ) Notice: Subject to any disclaimer, the term of this patent is extended or adjusted under 35 U.S.C. 154(b) by 183 days.

This patent is subject to a terminal disclaimer.

(21) Appl. No.: 15/319,940

(22) PCT Filed: Jun. 20, 2014

(86) PCT No.: PCT/AU2014/000649
§ 371 (c)(1),
(2) Date: Dec. 19, 2016

(87) PCT Pub. No.: WO2015/192162
PCT Pub. Date: Dec. 23, 2015

(65) Prior Publication Data
US 2017/0119571 A1  May 4, 2017

(51) Int. Cl.
*A61F 5/08* (2006.01)
*A61M 29/00* (2006.01)
(Continued)

(52) U.S. Cl.
CPC ............. *A61F 5/08* (2013.01); *A61M 15/085* (2014.02); *A61M 21/02* (2013.01); *A61M 29/00* (2013.01);
(Continued)

(58) Field of Classification Search
CPC ... A61F 5/08; A61F 5/56; A61B 17/24; A61B 2017/246; A61B 2017/248; A62B 23/06;
(Continued)

(56) References Cited

U.S. PATENT DOCUMENTS

| 851,048 A | * | 4/1907 | Woodward | A61F 5/08 606/199 |
| 1,034,566 A | | 8/1912 | Barratt | |

(Continued)

FOREIGN PATENT DOCUMENTS

| AU | 2013204827 A1 | 2/2014 |
| AU | 2013205674 A1 | 2/2014 |

(Continued)

OTHER PUBLICATIONS

International Preliminary Report on Patentability in PCT/AU2014/000649, dated Oct. 12, 2016, 5 pages.
(Continued)

*Primary Examiner* — Kathleen S Holwerda
(74) *Attorney, Agent, or Firm* — Servilla Whitney LLC

(57) ABSTRACT

A nasal dilator device comprises a substantially U-shaped body including a central portion arranged to span a septum of a nose when worn by a user and first and second leg members extending from the central portion in a first plane. The device further comprises a first cantilever rib member extending outward from the U-shaped body in a second plane and a second cantilever rib member extending outward from the U-shaped body in a third plane, wherein the first and second cantilever rib members extend away from each other. The device further comprises a first intermediate section connecting an end of the first leg member to a proximal end of the first cantilever rib member, wherein the first intermediate section extends between the first plane and second plane and a second intermediate section connecting an end of the second leg member to a proximal end of the second cantilever rib member, wherein the second intermediate section extends between the first plane and the third plane.

25 Claims, 14 Drawing Sheets

(51) Int. Cl.
*A61M 15/08* (2006.01)
*A61M 21/02* (2006.01)
*A61M 31/00* (2006.01)
*A61M 21/00* (2006.01)

(52) U.S. Cl.
CPC ..... *A61M 31/00* (2013.01); *A61M 2021/0016* (2013.01); *A61M 2205/75* (2013.01); *A61M 2210/0618* (2013.01)

(58) Field of Classification Search
CPC .... A61M 15/085; A61M 15/08; A61M 21/02; A61M 31/00; A61M 2021/0016; A61M 2210/0618; A61M 29/00; A61M 2205/75
USPC ............................ 606/204.45, 199; D24/135
See application file for complete search history.

(56) References Cited

U.S. PATENT DOCUMENTS

| | | | |
|---|---|---|---|
| 1,077,574 A * | 11/1913 | Woodward | A61F 5/08 606/199 |
| 1,255,578 A * | 2/1918 | Boxlely | A61F 5/08 606/199 |
| 1,481,581 A * | 1/1924 | Woodward | A61F 5/08 606/199 |
| 2,243,360 A * | 5/1941 | Slatis | A61M 15/08 128/206.11 |
| 3,710,799 A | 1/1973 | Caballero | |
| 3,722,509 A | 3/1973 | Nebel | |
| 3,905,335 A | 9/1975 | Kapp | |
| 4,414,977 A * | 11/1983 | Rezakhany | A61F 5/08 606/199 |
| 4,576,168 A | 3/1986 | Jalowayski | |
| 4,592,357 A | 6/1986 | Ersek | |
| 4,759,365 A | 7/1988 | Askinazy | |
| 5,059,193 A | 10/1991 | Kuslich | |
| 5,099,857 A | 3/1992 | Baldo et al. | |
| 5,423,858 A | 6/1995 | Bolanos et al. | |
| RE35,408 E * | 12/1996 | Petruson | A61F 5/08 128/858 |
| 5,683,465 A | 11/1997 | Shinn et al. | |
| 5,693,100 A | 12/1997 | Pisharodi | |
| 5,787,884 A | 8/1998 | Tovey | |
| 5,895,409 A | 4/1999 | Mehdizadeh | |
| 5,931,852 A * | 8/1999 | Brennan | A61F 5/08 606/199 |
| 5,955,376 A | 9/1999 | Tovey | |
| 6,109,262 A | 8/2000 | Tovey | |
| 6,129,763 A | 10/2000 | Chauvin et al. | |
| 6,270,512 B1 | 8/2001 | Rittmann | |
| 6,436,142 B1 | 8/2002 | Paes et al. | |
| 6,561,188 B1 | 5/2003 | Ellis | |
| 6,562,057 B2 | 5/2003 | Santin | |
| 6,626,179 B1 | 9/2003 | Pedley | |
| 6,821,298 B1 | 11/2004 | Jackson | |
| 6,978,781 B1 | 12/2005 | Jordan | |
| 7,055,523 B1 * | 6/2006 | Brown | A61F 5/08 128/206.11 |
| 7,105,008 B2 | 9/2006 | Maryanka | |
| 7,108,198 B2 * | 9/2006 | Altadonna, Jr. | A61K 9/0043 128/200.24 |
| 7,318,438 B2 * | 1/2008 | Brown | A61F 5/08 128/206.11 |
| 7,390,331 B2 | 6/2008 | Santin et al. | |
| D575,397 S * | 8/2008 | Noce | D24/135 |
| 7,461,651 B2 * | 12/2008 | Brown | A61F 5/08 128/200.24 |
| 7,727,252 B2 | 6/2010 | Maryanka | |
| 7,740,643 B2 | 6/2010 | Maryanka | |
| 7,918,224 B2 * | 4/2011 | Dolezal | A62B 23/06 128/205.27 |
| 8,048,102 B2 * | 11/2011 | Thomas | A61F 5/08 606/199 |
| D652,143 S * | 1/2012 | Brown | D24/135 |
| 8,262,688 B2 | 9/2012 | Santin et al. | |
| 8,403,954 B2 | 3/2013 | Santin et al. | |
| 8,491,622 B2 | 7/2013 | Brown | |
| 8,833,369 B2 | 9/2014 | Dolezal et al. | |
| 8,834,512 B1 * | 9/2014 | Brown | A61F 5/08 606/199 |
| D726,312 S | 4/2015 | Johnson | |
| D819,205 S * | 5/2018 | Snyder | D24/135 |
| 2003/0086825 A1 * | 5/2003 | Brennan | G01N 31/223 422/83 |
| 2003/0106555 A1 | 6/2003 | Tovey | |
| 2003/0144684 A1 | 7/2003 | Ogle | |
| 2004/0079814 A1 * | 4/2004 | Altadonna, Jr. | A61K 9/0043 239/34 |
| 2004/0111109 A1 * | 6/2004 | Ruiz | A61F 5/08 606/199 |
| 2005/0021073 A1 | 1/2005 | Santin et al. | |
| 2005/0278028 A1 | 12/2005 | Mujwid | |
| 2006/0185676 A1 * | 8/2006 | Brown | A61F 5/08 128/207.18 |
| 2006/0185677 A1 * | 8/2006 | Brown | A61F 5/08 128/207.18 |
| 2006/0207598 A1 * | 9/2006 | Thomas | A61F 5/08 128/206.11 |
| 2006/0259064 A1 * | 11/2006 | Maryanka | A61B 17/24 606/199 |
| 2006/0266367 A1 * | 11/2006 | Noce | A61F 5/08 128/207.18 |
| 2007/0107731 A1 * | 5/2007 | Reed | A61F 5/08 128/206.11 |
| 2008/0167676 A1 * | 7/2008 | Howard | A61F 5/56 606/199 |
| 2008/0178873 A1 * | 7/2008 | Alpers | A61F 5/08 128/200.24 |
| 2009/0194100 A1 | 8/2009 | Minagi | |
| 2009/0198268 A1 | 8/2009 | Case | |
| 2010/0042134 A1 | 2/2010 | Wien | |
| 2010/0063523 A1 | 3/2010 | Menard et al. | |
| 2010/0063532 A1 | 3/2010 | Moore | |
| 2010/0087749 A1 | 4/2010 | Tovey | |
| 2011/0118775 A1 * | 5/2011 | Brown | A61F 5/08 606/199 |
| 2012/0111340 A1 | 5/2012 | Robitaille | |
| 2012/0279504 A1 | 11/2012 | Moore | |
| 2012/0330345 A1 * | 12/2012 | Tasca | A61F 5/08 606/199 |
| 2013/0081637 A1 | 4/2013 | Foley | |
| 2013/0144325 A1 * | 6/2013 | Allegra | A61F 5/08 606/199 |
| 2013/0211275 A1 | 8/2013 | Curti | |
| 2013/0296809 A1 | 11/2013 | Santin et al. | |
| 2014/0128904 A1 * | 5/2014 | Mezzoli | A61F 5/08 606/199 |
| 2014/0246023 A1 * | 9/2014 | Maryanka | A61F 5/08 128/203.22 |
| 2015/0000675 A1 * | 1/2015 | Kallikounis | A61F 5/08 128/848 |
| 2015/0196420 A1 * | 7/2015 | Ede | A61M 31/002 604/285 |

FOREIGN PATENT DOCUMENTS

| | | |
|---|---|---|
| AU | 2013204827 B2 * | 11/2014 |
| CA | 2566268 A1 | 11/2004 |
| CN | 103520815 A | 1/2014 |
| EP | 1917993 A1 | 5/2008 |
| EP | 2387978 A2 | 11/2011 |
| EP | 2114326 B1 | 3/2014 |
| EP | 1968684 B1 | 2/2016 |
| JP | H11192251 A | 7/1999 |
| KR | 100893945 B1 | 4/2009 |
| WO | 88/09149 A1 | 12/1988 |
| WO | 96/06657 A1 | 3/1996 |
| WO | 96/07099 A1 | 3/1996 |
| WO | 99/36773 A1 | 7/1999 |
| WO | 00/78223 A1 | 12/2000 |

(56) References Cited

FOREIGN PATENT DOCUMENTS

| | | | |
|---|---|---|---|
| WO | 01/62342 A1 | 8/2001 | |
| WO | 02/31465 A1 | 4/2002 | |
| WO | 02/059569 A1 | 8/2002 | |
| WO | 2004026391 A1 | 4/2004 | |
| WO | 2007119041 A1 | 10/2007 | |
| WO | 2008/091782 A2 | 7/2008 | |
| WO | 2008109873 A2 | 9/2008 | |
| WO | 2009/124567 A1 | 10/2009 | |
| WO | 2011/104660 A2 | 9/2011 | |
| WO | 2012/137182 A2 | 10/2012 | |
| WO | WO-2012137182 A2 * | 10/2012 | ............... A61F 5/08 |
| WO | WO-2014015359 A1 * | 1/2014 | .......... A61M 31/002 |
| WO | 2014183966 A1 | 11/2014 | |

OTHER PUBLICATIONS

International Preliminary Report on Patentability in PCT/AU2015/050032, dated Dec. 20, 2016, 4 pages.
International Search Report in PCT/AU2014/000649, dated Sep. 18, 2014, 7 pages.
International Search Report in PCT/AU2015/050032, dated Apr. 17, 2015, 5 pages.
Written Opinion of the International Searching Authority in PCT/AU2014/000649, dated Sep. 18, 2014, 7 pages.
Written Opinion of the International Searching Authority in PCT/AU2015/050032, dated Apr. 17, 2015, 3 pages.
International Preliminary Report on Patentability in Int. Appln. No. PCT/AU2016/050621, completed Nov. 21, 2017, 22 pages.
International Search Report in Int. Appln. No. PCT/AU2016/050621, dated Oct. 25, 2016, 7 pages.
International Search Report in International Application No. PCT/AU2015/050314, dated Aug. 12, 2015, 4 pages.
Non-Final Office Action in U.S. Appl. No. 15/319,941, dated Apr. 11, 2018, 50 pages.
Written Opinion of the International Searching Authority in Int. Appln. No. PCT/AU2016/050621, dated Oct. 25, 2016, 7 pages.
Written Opinion of the International Searching Authority in International Application No. PCT/AU2015/050314, dated Aug. 12, 2015, 4 pages.
Airware Labs, retrieved from the internet Jul. 9, 2018, <URL: https://web.archive.org/web/20120522113321/http://www.airwarelab.com/>, published Mar. 22, 2012, 5 pages.
Breathe EZ Anti-Snoring Medical Nasal Device—Snoring Cure, retrieved from the internet on Jul. 9, 2018, <URL: https://web.archive.org/web/20120618221246/http://www.snoringcure.ca/breathe_ez_nasal_anti_snoring_medical_device.htm>, published May 14, 2007, 1 page.
Breathe-Aide, retrieved from the internet Jul. 9, 2018, <URL: https://web.archive.org/web/20141108204923/http://breatheaide.fm.alibaba.com/>, published Nov. 8, 2014, 1 page.
Breathe-Ezy Nasal Filters, retrieved from the internet Jul. 9, 2018, <URL: https://web.archive.org/web/20120615192635/http://www.breathe-ezy.com.au/>, published Apr. 29, 2005, 6 pages.
Breathing Relief Nasal Dilator, retrieved from the internet Jul. 9, 2018, <URL: https://web.archive.org/web/20120413210250/http://www.breathingrelief.com/>, published Jun. 16, 2006, 2 pages.
ClipAir® Anti-Snoring Nasal Dilator Device/Contre Ie Ronflement, retrieved from the internet on Jul. 9, 2018, <URL: https://web.archive.org/web/20120618061055/http://www.snoringcure.ca/clipair_nasal_anti_snoring_medical_dilator_device.htm>, published Aug. 1, 2010, 2 pages.
Flents Breathe Quiet! Nasal Dilator—Stop Snoring!, retrieved from the internet on Jul. 9, 2018, <URL: https://web.archive.org/web/20120425220535/http://www.amazon.com/Flents-Breathe-Quiet-Nasal-Dilator/dp/B0019IHLR2>, published Aug. 29, 2010, 4 pages.
Flents Breathe Well Nasal Dilator—The Alternative to Nasal Strips, retrieved from the internet Jul. 9, 2018, <URL: https://web.archive.org/web/20120411195907/http://www.amazon.com/Flents-Breathe-Well-Nasal-Dialator/dp/B001J4K5E2>, published Feb. 2, 2009, 4 pages.
Inhalclip, retrieved from the internet Jul. 9, 2018, <URL: https://web.archive.org/web/20120413113017/http://www.oscimedsa.com/Stress_insomnie_stop>, published Oct. 21, 2010, 3 pages.
International Preliminary Examination Report in PCT/AU2003/000504 dated Feb. 2, 2005, 36 pages.
Max-Air Nose Cones, retrieved from the internet Jul. 9, 2018, <URL: https://web.archive.org/web/20120725110753/http://www.maxaimosecones.com/max-air-nose-cones>, published Feb. 13, 2011, 8 pages.
Megavent Nasal Dilator, retrieved from the internet Jul. 9, 2018, <URL: http://www.wellnessproducts.ch/?lan=en&page=2&id=66999>, published Jun. 26, 2012, 3 pages.
Nasal Pass Dilator, retrieved from the internet Jul. 9, 2018, <URL: https://web.archive.org/web/20120630121946/http://nasalpass.com/contact_us.htm>, published Apr. 21, 2006, 1 pages.
Nasilator, The Science of Better Breating, retrieved from the internet Jul. 17, 2018, <URL: https://web.archive.org/web/20121219024329/http://www.nasilator.com/home.aspx>, published Sep. 6, 2012, 1 pages.
Non-Final Office Action in U.S. Appl. No. 10/631,415 dated Aug. 18, 2005, 15 pages.
Non-Final Office Action in U.S. Appl. No. 10/631,415 dated Dec. 29, 2005, 9 pages.
Non-Final Office Action in U.S. Appl. No. 11/363,884 dated May 14, 2009, 9 pages.
Non-Final Office Action in U.S. Appl. No. 11/363,924 dated Apr. 13, 2009, 9 pages.
Non-Final Office Action in U.S. Appl. No. 12/154,868 dated Oct. 23, 2014, 35 pages.
Noseglobes, retrieved from the internet Jul. 9, 2018, <URL:https://web.archive.org/web/20110128162352/http://noseglobes.com/>, published Jan. 28, 2011, 1 page.
Nozovent® Anti-Snoring Medical Nasal Dilator Device, retrieved from the internet on Jul. 9, 2018, <URL: https://web.archive.org/web/20120619012956/http://www.snoringcure.ca/nozovent_nasal_anti_snoring_medical_dilator_device.htm>, published Jul. 13, 2007, 2 pages.
Original Breathe Fit Snoring Aid Nasal Dilator, by Breathe Fit Nasal Dilator, retrieved from the internet on Jul. 9, 2018: <URL: https://web.archive.org/web/20120619035547/http://www.amazon.com/Original-Breathe-Fit-Nasal-Diiator/dp/B0012RMWC4>, published Aug. 21, 2009, 5 pages.
Sanispira Dpi, retrieved from the internet Jul. 9, 2018, <URL: https://web.archive.org/web/20120712044423/http://www.sanispira.it/eng/index.php>, published Mar. 4, 2011, 3 pages.
Sinus Cones, retrieved from the internet Jul. 9, 2018, <URL: https://web.archive.org/web/20120206054639/http://www.sanostec.com/code/productinfo.htm>, published Sep. 8, 2004, 2 pages.
SleepRight, retrieved from the internet Jul. 11, 2018, <URL: http://www.sleepright.com/nasal-breathe-aid.php>, published Jun. 17, 2013, 6 pages.
Snore Free, retrieved from the internet Jul. 9, 2018, <URL: https://web.archive.org/web/20120614222005/http://www.magnetictherapy.co.uk/scp/SPECIALITY_PRODUCTS/SNORE_FREE.html>, published Dec. 8, 2004, 2 pages.
Snore Pin, Sleep Apnea Snoring Treatment, retrieved from the internet Jul. 17, 2018, <URL: https://web.archive.org/web/20130111010828/http://omnisleep.in/snore-pin.html>, published Jan. 11, 2013, 2 pages.
Snoreben, retrieved from the internet Jul. 9, 2018, <URL: http://www.benmedical.com.au/>, published Jan. 2011, 2 pages.
Snoregem, British Snoring & Sleep Apnoea Associate, retrieved from the internet Jul. 9, 2018, <URL: https://web.archive.org/web/20120627060249/http://www.britishsnoring.co.uk/shop/snoregem.php>, published Jul. 3, 2010, 2 pages.
Snore-no-More, retrieved from the internet Jul. 9, 2018, <URL: https://web.archive.org/web/20120626140524/http://www.britishsnoring.co.uk/shop/nasal_dilators/snore_no_more.php?>, published Dec. 12, 2005, 1 pages.

(56) References Cited

OTHER PUBLICATIONS

Surgical Nostril Retainers, Porex Surgical Products Group, retrieved from the internet Jul. 17, 2018, <URL: https://web.archive.org/web/20051217233845/https://www.porexsurgical.com/English/surgical/sprodnoseother.asp>, published Dec. 19, 2005, 2 pages.
Ultimate Nasal Dilator, retrieved from the internet Jul. 9, 2018, <URL: https://web.archive.org/web/20120718070024/http://www.nasalaid.com/>, published Oct. 28, 2007, 1 page.
WoodyKnows—Super Nasal Filter for Allergy Relief, retrieved from the internet Jul. 17, 2018, <URL: https://web.archive.org/web/20120818163139/http://www.woodyknows.com:80/>, published Aug. 18, 2012, 3 pages.
Final Office Action in U.S. Appl. No. 15/319,941, dated Mar. 3, 2020, 40 pages.
Non-Final Office Action in U.S. Appl. No. 15/579,304, dated Jan. 24, 2020, 20 pages.
Final Office Action in U.S. Appl. No. 15/579,304, dated Jan. 21, 2021, 13 pages.
Non-Final Office Action in U.S. Appl. No. 15/748,698, dated Mar. 22, 2021, 26 pages.
Non-Final Office Action in U.S. Appl. No. 15/579,304 dated Aug. 21, 2020, 12 pages.

\* cited by examiner

NASAL DILATOR DEVICES

CROSS REFERENCE TO RELATED APPLICATIONS

This is a National Phase entry of International Application No. PCT/AU2014/000649, filed Jun. 20, 2014, the disclosure of which is incorporated herein by reference in its entirety.

TECHNICAL FIELD

Described embodiments generally relate to nasal dilator devices for facilitating respiration. Some embodiments relate to nasal dilator devices to be fitted to the nose to facilitate or improve respiration during sleeping and/or sporting activities and/or for general day-to-day wear. Some embodiments relate to nasal dilator devices including filtration mechanisms to filter airflow during respiration and other embodiments relate to nasal dilator devices including agent delivery mechanisms for delivery of fragrances and/medicaments to the nose during respiration.

BACKGROUND

Nasal dilator devices are worn by users to dilate their nasal cavities when sleeping and/or partaking in sporting activities to thereby facilitate respiration. However, many nasal dilator devices are uncomfortable to wear and/or become easily dislodged from a user's nose during such activities.

It is desired to address or ameliorate one or more shortcomings of prior nasal dilator devices, or to at least provide a useful alternative thereto.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application

SUMMARY

Some embodiments relate to a nasal dilator device comprising: a substantially U-shaped body including: a central portion arranged to span a septum of a nose when worn by a user; and first and second leg members extending from the central portion in a first plane; a first cantilever rib member extending outward from the U-shaped body in a second plane; a second cantilever rib member extending outward from the U-shaped body in a third plane; wherein the first and second cantilever rib members extend away from each other; a first intermediate section connecting an end of the first leg member to a proximal end of the first cantilever rib member, wherein the first intermediate section extends between the first plane and second plane; and a second intermediate section connecting an end of the second leg member to a proximal end of the second cantilever rib member, wherein the second intermediate section extends between the first plane and the third plane.

In some embodiments, the first and second cantilever rib members may be arcuate cantilever rib members, each having a curvature along its length. In some embodiments, the first and second intermediate sections are arcuate intermediate sections, each having a curvature along its length.

The first and second intermediate sections may be arranged, in use, to extend along a length of the septum and the first and second cantilever rib members may be each arranged, in use, to extend from a floor of a respective nasal orifice to an inner wall of the nostrils.

In some embodiments, the first and second intermediate portions may extend obtusely from the ends of the first and second leg members. The second and third planes may be converging planes. In some embodiments, the first and second cantilever rib members may exhibit an elongate arched profile which approximates at least a portion of one of a circle, ellipse or parabola.

In some embodiments, the first and second leg members may be inclined towards each other such that a relatively greater distance is provided between the first and second leg members towards the central portion to accommodate a columella of a nose when donned by the user. In some embodiments, the first and second intermediate sections may be inclined away from each other to assist in urging the respective first and second cantilever rib members against inner walls of respective nostrils when worn by the user.

The first and second cantilever rib members may comprise respective first and second nostril engaging elements for engaging with an inner wall of a respective nostril. The first and second nostril engaging elements may be disposed at distal ends of the first and second cantilever rib members, respectively. Enlarged pads may be disposed on the first and second nostril engaging elements to engage with inner walls of the nostrils.

In some embodiments, the nasal dilator device may further comprise a first and second releasable attachment mechanism for releasably attaching the first and second cantilever rib members, respectively, to the U-shaped body. For example, the releasable attachment mechanisms may be arranged to releasably attach the first and second nostril engaging elements to the first and second leg members, respectively. In some embodiments, the releasable attachment mechanisms may be arranged to releasably attach the first and second nostril engaging elements to the first and second intermediate sections, respectively.

The releasable attachment mechanisms may each comprise an arm and a socket arranged to receive and engage the arm. A stopper may be disposed at an end of the arm to hinder the arm from withdrawing from the socket. In one embodiment, the arms may be disposed on an inner surface of first and second nostril engaging elements of the first and second cantilever rib members, respectively, and the sockets may be disposed on the first and second leg members. In another embodiment, the arms may be disposed on an inner surface of first and second nostril engaging elements of the first and second cantilever rib members, respectively, and the sockets may be disposed on the first and second intermediate sections. In another embodiment, the sockets may be disposed on an inner surface of first and second nostril engaging elements of the first and second cantilever rib members, respectively, and the arms may be disposed on the first and second leg members. In another embodiment, the sockets may be disposed on an inner surface of first and second nostril engaging elements of the first and second cantilever rib members, respectively, and the arms may be disposed on the first and second intermediate sections.

In some embodiments, a capsule may be provided within the socket and may be arranged to be activated by the arm when the arm is received by the socket. The capsule may include at least one of a medicament or compound. The arm may comprise a coating disposed thereon arranged to release a scent in response to abrasion of the coating. An aperture may be disposed in each of the first and second nostril engaging elements. The aperture may be arranged to receive at least one of a compound, a medicament, and a capsule comprising a medicament or compound emanating a scent.

Some embodiments relate to a nasal dilator device a nasal dilator device comprising: a substantially U-shaped body including: a central portion arranged to span a septum of a nose when worn by a user; and first and second leg members extending from the central portion in a first plane; a first closed loop structure extending outward from a longitudinal axis of the U-shaped body in a second plane and defining a first aperture; a second closed loop structure extending outward from a longitudinal axis of the U-shaped body in a third plane and defining a second aperture; wherein the first and second closed loop structures extend away from each other; a first intermediate section connecting an end of the first leg member to a proximal end of the first loop structure, wherein the first intermediate section extends between the first plane and second plane; and a second intermediate section connecting an end of the second leg member to a proximal end of the second loop structure, wherein the second intermediate section extends between the first plane and the third plane.

In some embodiments, the first loop structure may comprise a first flange portion and the second loop structure may comprise a second flange portion, wherein the first and second flange portions are arranged to form a seal with the walls nasal passage in use.

In some embodiments, the first and second loop structures may each comprise a filter spanning the first and second apertures defined by the first and second loop structures. The filters may be arranged to snap fit into the first and second loop structures. The filters may be welded to the first and second loop structures.

In some embodiments, the first and second intermediate sections are arcuate intermediate sections, each having a curvature along its length. The first and second intermediate portions may extend obtusely from the ends of the first and second leg members.

The first and second intermediate sections may be arranged, in use, to extend along a length of the septum and the first and second loop structures may be each arranged, in use, to extend from a floor of a respective nasal orifice along an inner wall of the nostrils such that the first and second apertures are aligned with a nasal passage of the nose.

In some embodiments, the second and third planes may be converging planes.

The first and second leg members may be inclined towards each other such that a relatively greater distance is provided between the first and second leg members towards the central portion to accommodate a columella of a nose when donned by the user. The first and second intermediate sections may be inclined away from each other to assist in urging the respective first and second loop structures against inner walls of respective nostrils when worn by the user.

In some embodiments, the nasal dilator device may further comprise a film disposed on a surface of the nasal dilator and a removable seal provided on the film to mitigate release of a compound from the film.

In some embodiments, the nasal dilator device may further comprise an overmould disposed on at least one of the central portion, the leg members, the intermediate sections and the arcuate cantilever rib members. The overmould may be infused with a compound, a medicament, a fragrance or an aroma. The nasal dilator device may be composed of a substrate material infused with a medicament, a fragrance or an aromatic agent.

In some embodiments, the central portion comprises a tab extending in a direction substantially opposite to the first and second leg members to assist with insertion, removal and/or placement of the nasal dilator device. The tab may be removeable from the nasal dilator device.

Some embodiments relate to a nasal dilator device comprising a substantially U-shaped body including: a central portion arranged to span a septum of a nose when worn by a user; and first and second leg members extending from the central portion; first and second cantilever rib members extending outward from a longitudinal axis of the U-shaped body and away from one another; a first intermediate section connecting an end of the first leg member to a proximal end of the first cantilever rib member; and a second intermediate section connecting an end of the second leg member to a proximal end of the second cantilever rib member; wherein the first and second leg members are arranged, in use, to extend inward of respective nasal orifices along the septum, the first and second intermediate sections are arranged, in use, to extend along a length of the septum behind the columella and alar fibrofatty tissue of the nose and the first and second cantilever rib members are each arranged, in use, to extend from a floor of the respective nasal orifices to an inner wall of the nostrils.

BRIEF DESCRIPTION OF DRAWINGS

Embodiments are described in further detail below, by way of example, with reference to the accompanying drawings, in which.

DESCRIPTION OF EMBODIMENTS

Figure 1A:
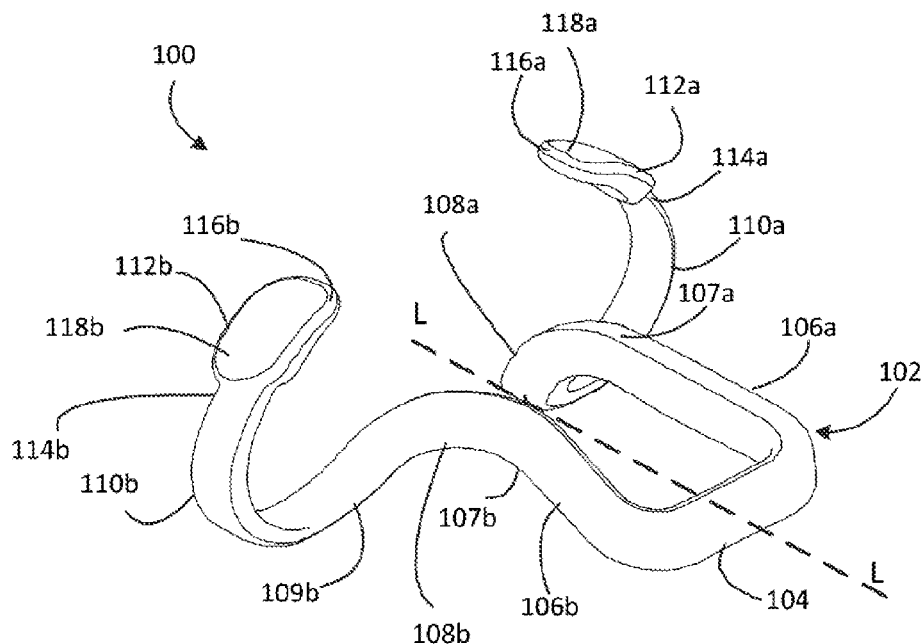
FIG. 1A is front perspective view of a nasal dilator device according to some embodiments.

Described embodiments generally relate to nasal dilator devices for facilitating respiration. Some embodiments relate to nasal dilator devices to be fitted to the nose to facilitate or improve respiration during sleeping and/or sporting activities and/or for general day-to-day wear. Some embodiments relate to nasal dilator devices including filtration mechanisms to filter airflow during respiration and other embodiments relate to nasal dilator devices including agent delivery mechanisms for delivery of fragrances and/or medicaments to the nose during respiration.

Referring to FIG. 1A to 1E, there is illustrated a nasal dilator device, generally indicated at 100 and substantially symmetrical about a longitudinal axis L, according to some embodiments. The nasal dilator device 100 comprises a generally U-shaped body 102 having a central portion 104 and first and second leg members, 106a and 106b, respectively, extending from the central portion 104 in a first plane P1.

The nasal dilator device comprises a first intermediate section 108a extending from an end 107a of the first leg member 106a and a second intermediate section 108b extending from an end 107b of the second leg member 106b. In some embodiments, and as depicted in FIGS. 1A to 1E, the first and second intermediate portions 108a, 108b, may be curved or arcuate along their length. In other embodiments, the first and second intermediate portions 108a, 108b may be substantially straight along their length or may comprise a plurality of angled or arcuate portions. For example, the first and second intermediate portions 108a, 108b may extend obtusely from the first and second ends 107a, 107b, for example, substantially at an angle of between approximately 95° and 130° to the longitudinal axis. For example, the first and intermediate sections 108a, 108b may deviate by approximately 100° from the longitudinal axis.

Referring again to FIGS. 1A to 1E, the nasal dilator device 100 comprises a first rib member 110a projecting from the first intermediate section 108a in a second plane P2 and a second rib member 110b projecting from the second intermediate section 108b in a third plane P3. In some embodiments, the first and second rib members 110a, 110b may project substantially outward or laterally of the longitudinal axis of the U-shaped body 102. For example, the first and second rib members 110a, 110b may be cantilever rib members that extend from the first and second intermediate sections 108a, 108b, respectively outwardly from the longitudinal axis and away from one another in a substantially cantilever manner. In some embodiments, the first and second rib members 110a, 110b may be arcuate rib members 110a, 110b or arcuate cantilever rib members 110a, 110b.

In some embodiments, the first and second rib members 110a, 110b may exhibit an elongate arched or bow-like profile which may approximate at least a portion of a circle, ellipse or parabola. For example, the first and second rib members 110a, 110b may extend arcuately along the second and third planes, P2 and P3, respectively in a direction substantially toward the first plane P1.

Figure 1B:
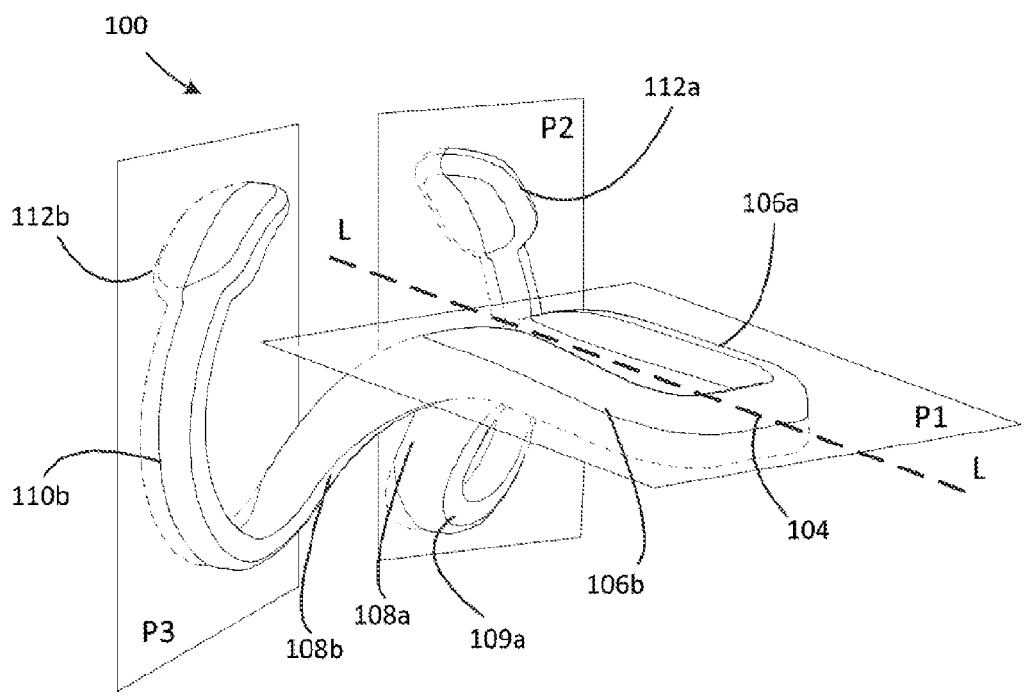
FIG. 1B is a further front perspective view of the nasal dilator device of FIG. 1A.
Figure 1C:
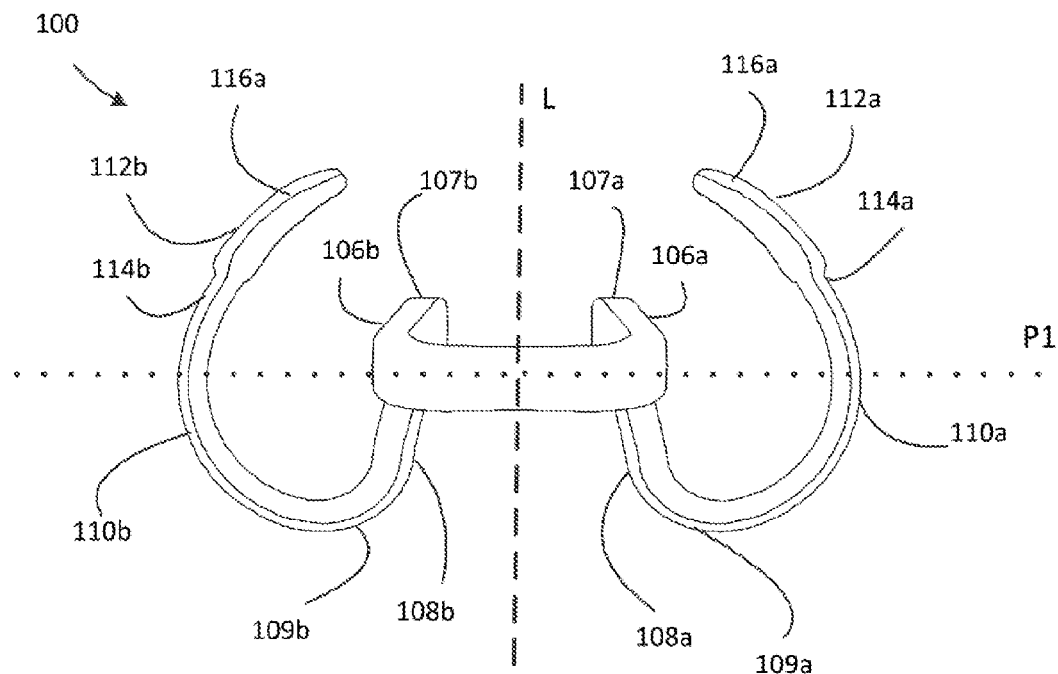
FIG. 1C is a front view of the nasal dilator device of FIG. 1A.
Figure 1D:
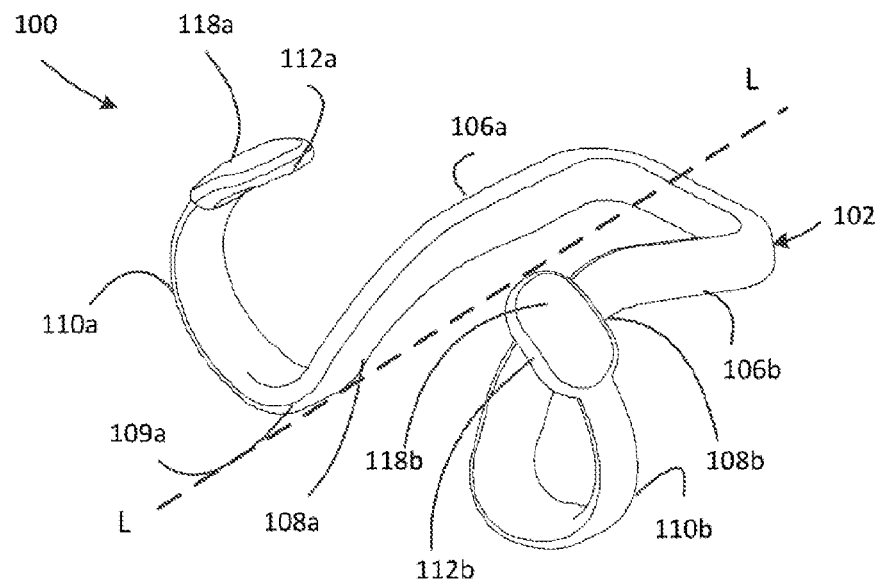
FIG. 1D is a rear perspective view of the nasal dilator device of FIG. 1A.
Figure 1E:
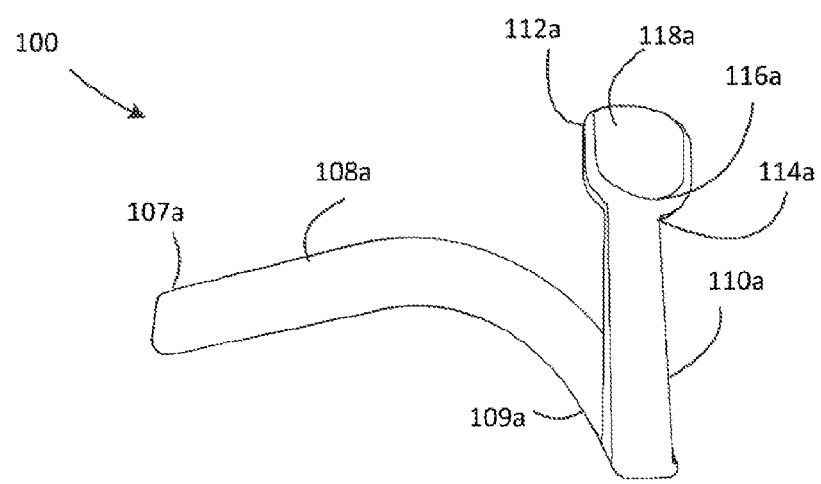
FIG. 1E is a partial side view of the nasal dilator device of FIG. 1A.

The first and second rib members 110a. 110b may be flexible and resiliently biased away from the first and second intermediate sections 108a, 108b, respectively, to allow the first and second rib members 110a, 110b to be compressed for insertion into the nose of a user and to reform once placed inside the nose to thereby dilate the nostrils as discussed in more detail below with reference to FIGS. 3A and 3B. As best depicted in FIGS. 1A and 1B, the first intermediate section 108a may extend or transition between the first plane P1 and the second plane P2 to interconnect the end 107a of the first leg member 106a to a proximal end 109a of the first rib member 110a and the second intermediate section 108b may extend or transition between the first plane and the third plane to interconnect the end 107b of the second leg member 106b to a proximal end 109b of the second rib member 110b.

In some embodiments, the configuration of the first and second intermediate sections 108a, 108b may be associated with an orientation or location of the first and second rib members 110a, 110b with respect to the U-shaped body 104. For example, the configuration of the first and second intermediate sections 108a, 108b may dictate or define an angle between the first plane P1 and the second plane P2 and between the first plane P1 and the third plane P3, respectively. The second and third planes, P2 and P3, may each form an acute angle, a right angle, or substantially right angle or an obtuse angle with the first plane P1. For example, the second and third planes P2 and P3, may be converging planes and may each form an obtuse angle of approximately 95° to 130° with the first plane P1 such that the first and second intermediate sections 108a 108b take the form of obtuse arcuate sections. In some embodiments, the first, second and third planes, P1, P2, P3 may be different from each other and in some embodiments, the second and third planes, P2, P3 may be the same plane and may be different to the first plane P1.

The first and second intermediate sections 108a. 108b may be inclined away from or diverge from one another to assist in urging the respective first and second rib members 110a, 110b against inner walls of respective nostrils when worn by the user.

As depicted in FIGS. 1A to 1E, the first and second rib members 110a, 110b, of the nasal dilator device 100 may comprise respective first and second nostril engaging elements, 112a and 112b, disposed at distal ends 114a, 114b, of the first and second arcuate rib members 110a, 110b, respectively, for engaging with inner walls of respective nostrils when worn by a user. In some embodiments, the first and second nostril engaging elements, 112a, 112b may comprise relatively large surface areas 116a, 116b with respect to the first and second arcuate rib members 110a, 110b.

In some embodiments, the first and second nostril engaging elements 112a, 112b may have pads 118a, 118b, disposed thereon, to engage with the inner walls of the nostrils. For example, the pads 118a, 118b may be disposed on the relatively large major surface areas 116a, 116b of the nostril engaging elements, 112a and 112b and may be enlarged with respect to the first and second arcuate rib members 110*a*, 110*b*, and/or the nostril engaging elements, 112*a* and 112*b*.

Figure 2:
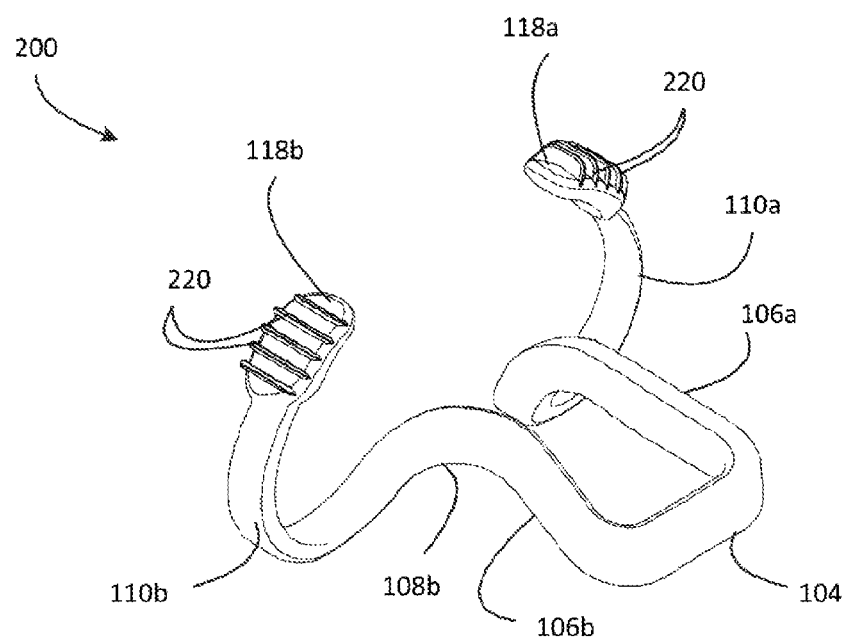
FIG. 2 is a front perspective view of a nasal dilator device including fin-like structures disposed thereon, according to some embodiments.

Referring now to FIG. 2, there is illustrated a nasal dilator device, generally indicated at 200, according to some embodiments. The nasal dilator device 200 may comprise similar components and elements to those of nasal dilator device 100 depicted in FIGS. 1A to 1E and accordingly those similar components and elements are denoted like numerals.

In some embodiments, as depicted in FIG. 2, the pads 118*a*, 118*b* of the nasal dilator device 200 may be composed of a relatively soft overmould material, for example a polymer material such as thermoplastic elastomer (TPE) and/or may be provided with a series of protrusions, fins or fin-like structures 220 to provide a comfortable and/or grippable surface for engaging with the inner walls of the nostrils. In some embodiments, such an overmould material may be provided on at least a portion of the rib members 110*a*, 110, and/or on at least a portion of the intermediate sections 108*a*, 108*b*.

The nasal dilator device 100, 200 may be configured to be orientated in a manner such that the first and second nostril engaging elements 112*a*, 112*b* may be positioned at a junction of the greater alar cartilage and lateral nasal cartilage, providing improved support for dilation of the nasal passage 308, as discussed in more detail with reference to FIGS. 3A and 3B below.

Figure 3A:
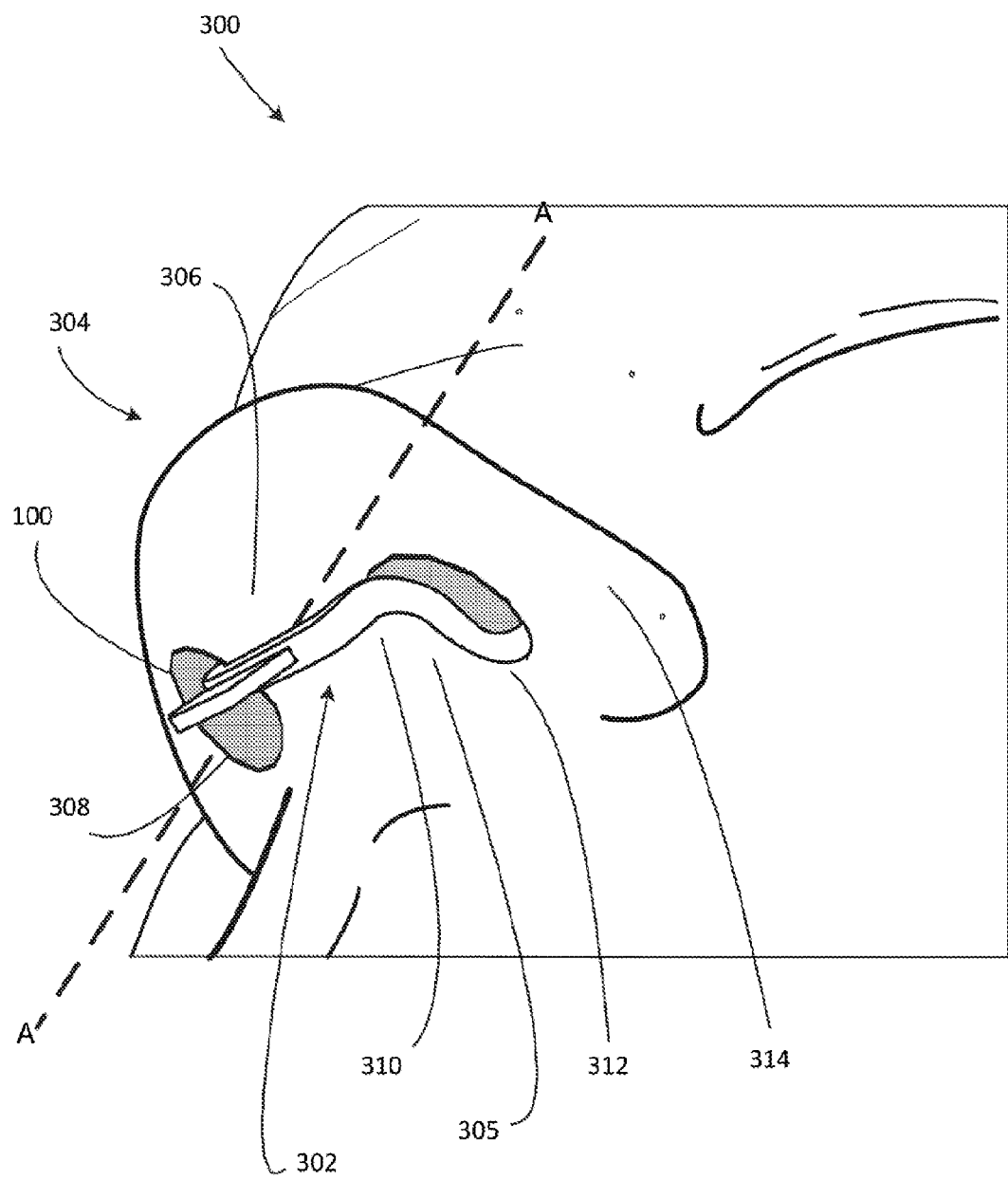
FIG. 3A is a perspective view of a user donning the nasal dilator device of FIGS. 1A to 1E.
Figure 3B:
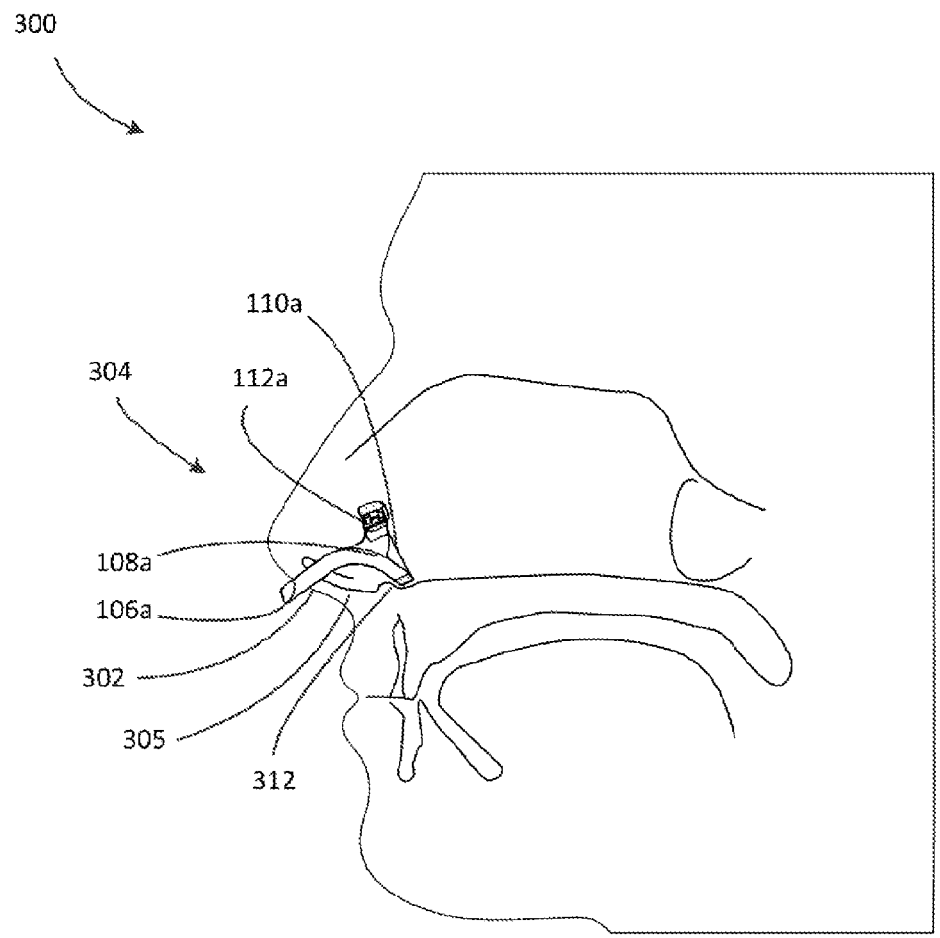
FIG. 3B is a side view of the user of FIG. 3A.

FIG. 3A is a perspective view of a user, generally indicated at 300, wearing or donning the nasal dilator device 100 of FIG. 1A and FIG. 3B is a cross sectional view taken along a midline A-A of the nose of the user of FIG. 3A.

As depicted in FIGS. 3A and 3B, the nasal dilator device 100 is configured to be orientated such that the central portion 104 spans a septum 302, and in particular, a columella 310 (the terminal section or fleshy external end of the septum) of a nose 304 and is positioned toward a tip 306 of the nose 304 and the first and second leg members 106*a*, 106*b* extend inward, along a nasal passage 308. For example, the first and second leg members 106*a*, 106*b*, may extend inward at an angle of approximately 30 to 40 degrees to a midline A-A of the nose 304. The first and second intermediate sections 108*a*, 108*b* may extend along a length of the septum 302 behind the columella 310 and the fibrofatty tissue 305 or bulbous region around the base of the nostrils 314 and the first and second rib members 110*a*, 110*b*, each may extend from a floor 312 of the nasal passage 308 behind the columella 310 and the fibrofatty tissue 305 or bulbous region around the base of the nostrils 314 to an inner wall (not shown) of the nostrils 314. In this way, the nasal dilator device 100 may be securely retained within the nose 304 with little or no pinching of or pressure being exerted on the septum 302. Furthermore, the ergonomic shape of the intermediate portions 108*a*, 108*b* allows the nasal dilator device to sit within the nose in a manner that may accommodate various shapes and sizes of noses, including those having hanging columellas 310.

In some embodiments, the first and second rib members 110*a*, 110*b* of the nasal dilator device 100 are composed of a flexible material and are generally squeezed or compressed by a user into a compressed state to allow insertion into the nasal passages 308 of the nose 304. The first and second rib members 110*a*, 110*b* may be biased to reform or revert to a natural uncompressed state and once inserted into the nasal passage 308, the first and second rib members 110*a*, 110*b* may each exert an outward force on the inner wall (not shown) of the nostril 314 and on the floor 312 of the nose 304, to thereby dilate the nasal passage 308. Thus, as opposed to exerting pressure on the septum 302 to dilate the nasal passage 308, the intermediate portions 108*a*, 108*b*, of nasal dilator device 100 are effective to cause the first and second rib members 110*a*, 110*b* to use the floor 312 of the nose 304 as a support structure for dilation of the nostrils 314. By using the floor 312 of the nose 304 as a support structure or anchor from which the first and second rib members 110*a*, 110*b* may launch or push off from, any pinching or exertion of force on the septum may be mitigated or avoided and a more comfortable and natural or anatomical fit may be achieved.

The nasal dilator device 100 is configured to cooperate with internal contours of the nose 304 and sit securely and comfortably in the nose, whilst mitigating obstruction of air flow through the nasal passage 308. For example, the rib members 110*a*, 110*b*, may be curved or arcuate along their length to correspond with the internal contours of the nose 304 and provide a more comfortable fit. In some embodiments, the first and second leg members 106*a*. 106*b* may be inclined toward each other or converge such that a relatively greater distance is provided between the first and second leg members 106*a*, 106*b* towards the central portion 104 in order to accommodate the columella 310 and to assist in holding the nasal dilator device 100 in place when worn.

Referring now to FIGS. 4A to 4D, there is illustrated a nasal dilator device, generally indicated at 400, according to some embodiments. The nasal dilator device 400 may comprise similar components and elements to those of nasal dilator device 100 depicted in FIGS. 1A to 1E and accordingly those similar components and elements are denoted like numerals.

In addition to those similar components and elements of nasal dilator device 100, nasal dilator device 400 may comprise a first and second releasable attachment mechanism 402*a* and 402*b*, respectively. The first and second releasable attachment mechanism 402*a*, 402*b* may comprise mating or interlocking components and may be employed to releasably attach the first and second rib members, 110*a* and 110*b*, respectively, to the U-shaped body 102, to thereby define first and second adjustable looped structures, 411*a*, and 411*b*, respectively.

In some embodiments, the first and second releasable attachment mechanisms 402*a*. 402*b* may comprise respective arms 404*a*, 404*b*, such as pins or ratchets, extending from respective reverse or inner surfaces 406*a*, 406*b* of the first and second nostril engaging elements 112*a*, 112*b*. The first and second releasable attachment mechanisms 402*a*, 402*b* may comprise respective sockets 408*a*, 408*b* for receiving and/or engaging the respective arms 404*a*, 404*b*. The first and second releasable attachment mechanisms 402*a*, 402*b* may be configured to allow a user to selectively adjust a degree of dilation or expansion and contraction of the first and second rib members 110*a* and 110*b* with respect to the U-shaped body 102.

Figure 4A:
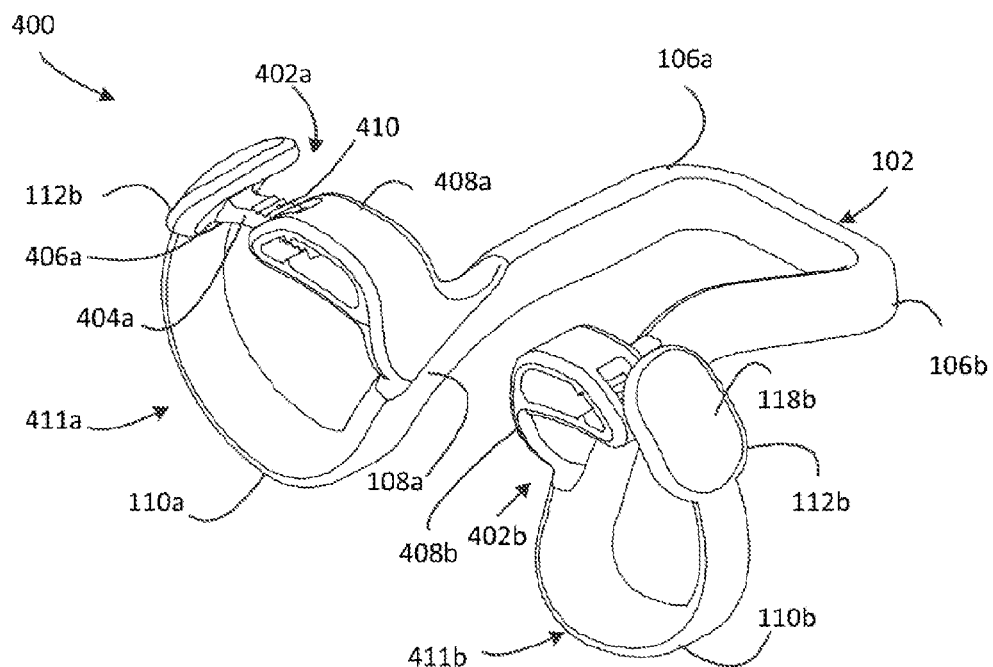
FIG. 4A is a rear perspective view of a nasal dilator device according to some embodiments.
Figure 4B:
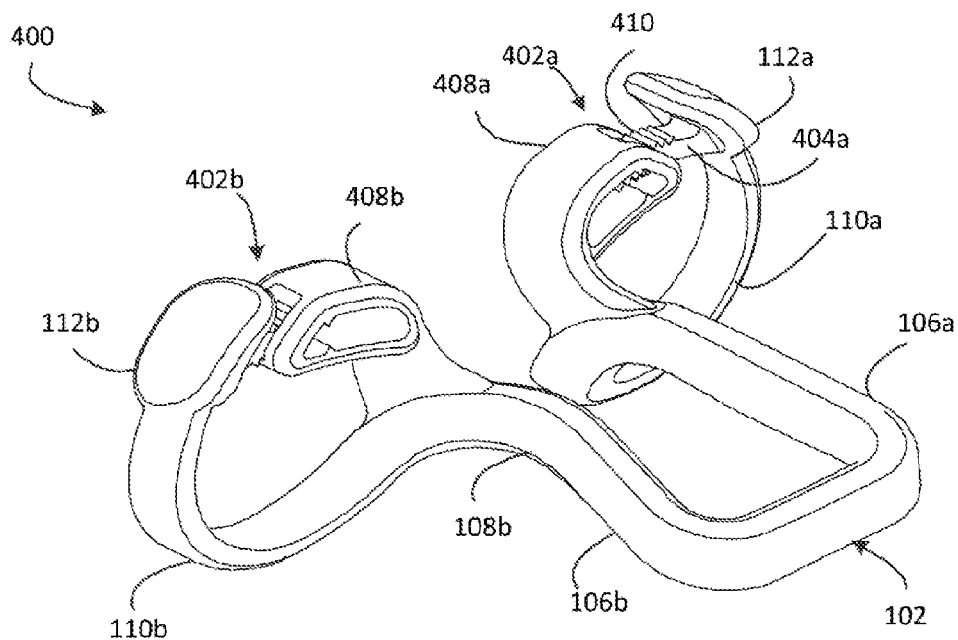
FIG. 4B is a front perspective view of the nasal dilator device of FIG. 4A.
Figure 4C:
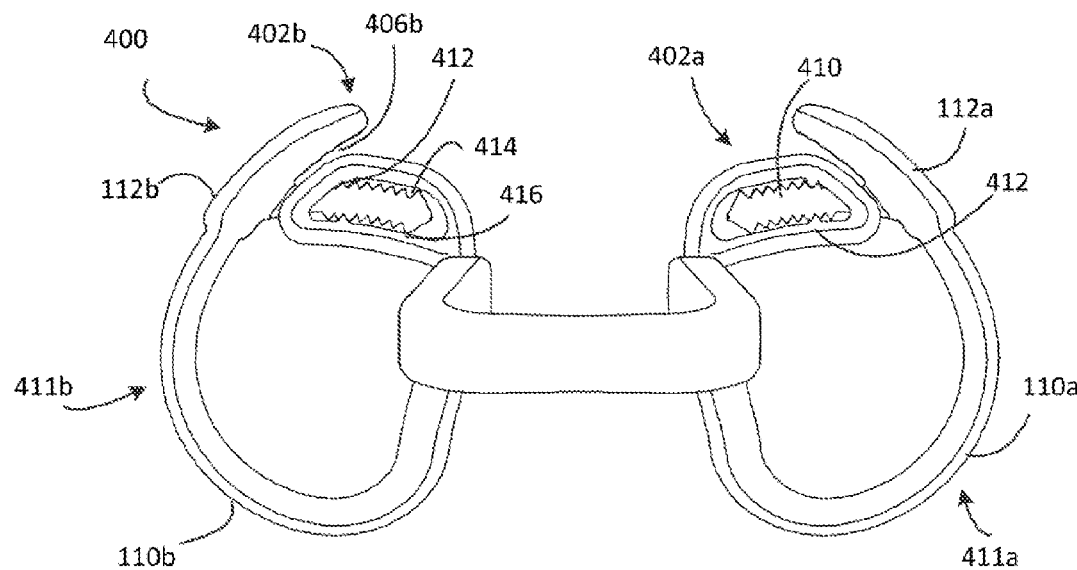
FIG. 4C is a front view of the nasal dilator device of FIG. 4A in a closed configuration.
Figure 4D:
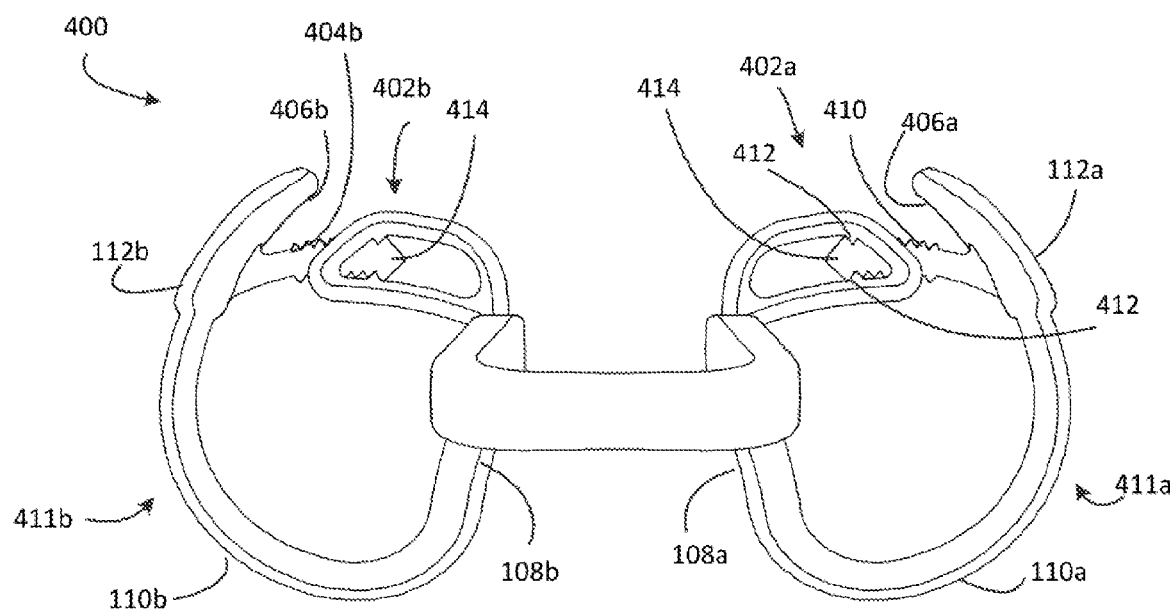
FIG. 4D is a front view of the nasal dilator device of FIG. 4A in a partially closed configuration.

For example, and as best illustrated in FIGS. 4C and 4D, the arms 404*a*, 404*b* may include at least one of or a series of serrations, detents or protrusions 410 arranged to engage with at least one or a series of grooves or ridges 412 provided on or within the sockets 408*a*, 408*b*. For example, the grooves or ridges 412 may extend downwardly from a upper jaw portion 414 of the sockets 408*a*, 408*b* and/or may extend upwardly from a lower jaw portion 416.

Figure 5:
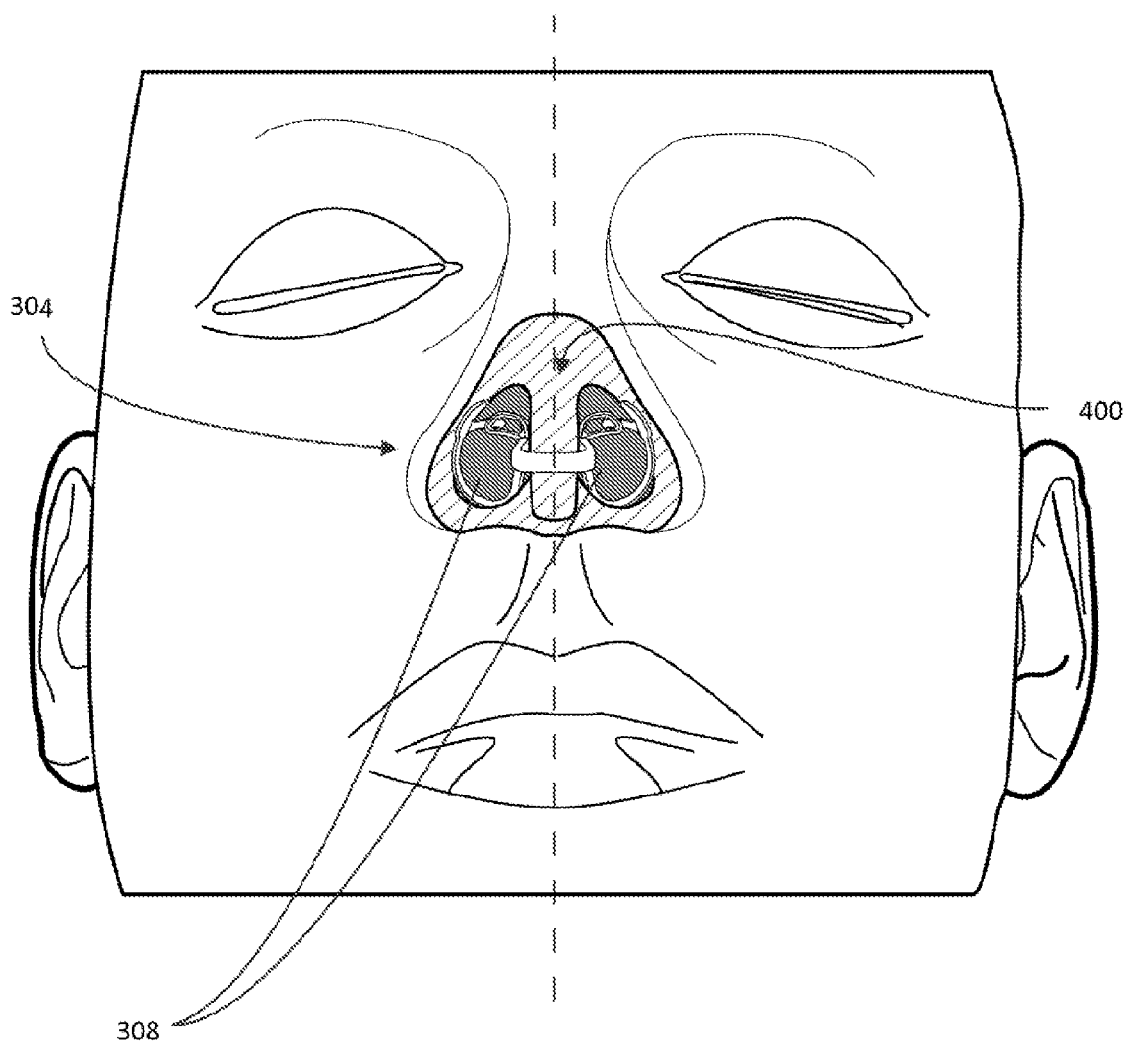
FIG. 5 is a front perspective view of a user donning the nasal dilator device of FIGS. 4A to 4D.

Application of sufficient force by a user to the first and second releasable attachment mechanisms 402*a*, 402*b* may be effective to move the arms 404*a*, 404*b* with respect to the sockets 408*a*, 408*b* and overcome a restrictive force between the detents 410 and the grooves 412 to allow the detents 410 and/or the grooves 412 to deform and the degree or level of dilation to be adjusted. The engagement of the detents 410 with the grooves 412 may provide a sufficient restrictive force to hold the arms 404a, 404b fixed when provided in the nose 304, as depicted in FIG. 5.

The arms 404a, 404b may comprise stoppers 414 at their ends to prevent or hinder the arms 404a, 404b from disengaging from or withdrawing from the respective sockets 408a, 408b. For example, application of a relatively large pulling force may be sufficient to cause the arms 404a, 404b to withdraw from the sockets 408a, 408b. In some embodiments, the stoppers 414 may be arrow shaped.

In some embodiments, the sockets 408a, 408b may be disposed on the first and second intermediate sections 108a, 108b and extend therefrom towards the respective arms 404a, 404b. The releasable attachment mechanisms 402a, 402b may be arranged to releasably attach or lock the first and second nostril engaging elements 112a, 112b to the first and second intermediate sections 108a, 108b.

In other embodiments, the sockets 408a, 408b may be disposed on the first and second leg members 106a, 106b and extend therefrom towards the respective arms 404a, 404b. The releasable attachment mechanisms 402a, 402b may be arranged to releasably attach or lock the first and second nostril engaging elements 112a, 112b to the first and second leg members 106a, 106b.

In other embodiments, the sockets 408a, 408b may be disposed on the first and second rib members 110a, 110b and extend therefrom towards the respective arms 404a, 404b. The attachment mechanisms 402a, 402b may be arranged to releasably attach or lock the first and second nostril engaging elements 112a, 112b to the first and second rib members 110a, 110b.

In other embodiments, the first and second releasable attachment mechanisms 402a, 402b may comprise respective sockets 408a, 408b, extending from the respective reverse or inner surfaces 406a, 406b, of the first and second nostril engaging elements 112a. 112b and respective arms 404a, 404b extending from the first and second intermediate sections 108a, 108b, the first and second leg members 106a, 106b, or the first and second rib members 110a, 110b.

As illustrated in FIG. 4C, the arms 404a, 404b may be fully or substantially fully inserted into the respective sockets 408a, 408b to enable the nasal dilator device 400 to adopt or assume a fully closed or substantially fully closed state, to thereby tighten or contract the looped structures 411a, 411b.

As illustrated in FIG. 4D the arms 404a, 404b may be partially inserted into the sockets 408a, 408b to enable the nasal dilator device 400 to adopt or assume a partially closed state, to provide for looser or less tight looped structures 411a, 411b and accommodate variations in nasal passage sizes.

Figure 6A:
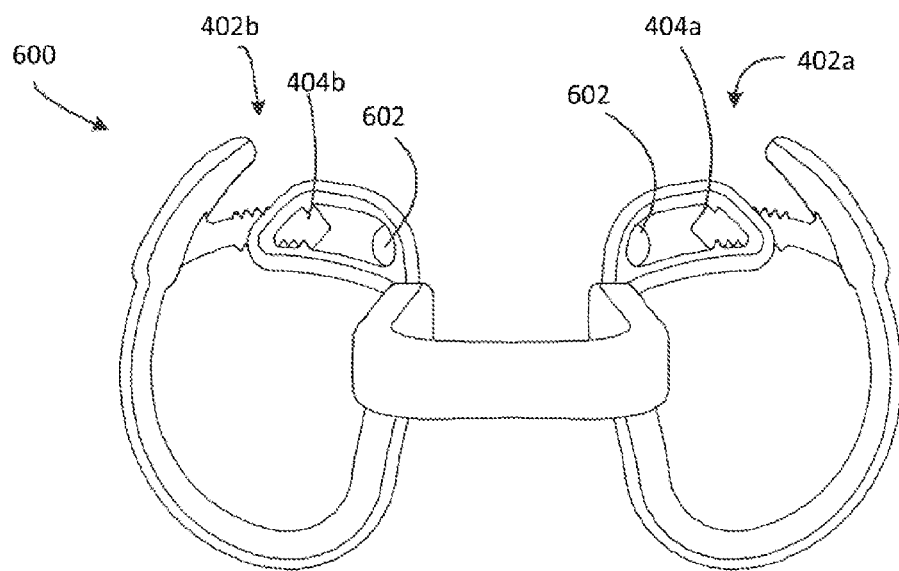
FIG. 6A is a front view of a nasal dilator device in a partially closed configuration, wherein the nasal dilator device includes a capsule, according to some embodiments.
Figure 6B:
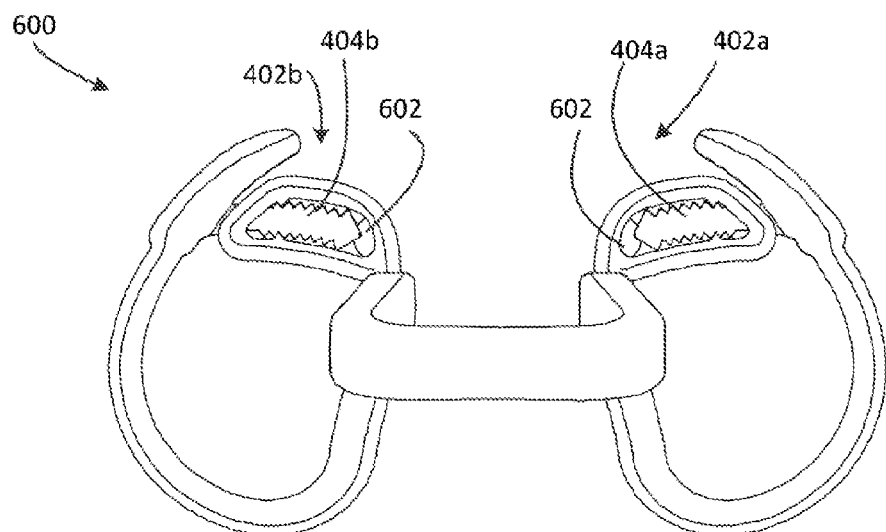
FIG. 6B is a front view of a nasal dilator device of FIG. 6A in a closed configuration.

Referring to FIGS. 6A and 6B, there is depicted a nasal dilator device 600 according to some embodiments. The nasal dilator device 600 may comprise similar components and elements to those of nasal dilator device 400 depicted in FIGS. 4A to 4D and accordingly those similar components and elements are denoted like numerals.

The nasal dilator device 600 comprises at least one capsule 602 disposed within respective sockets 408a. 408b. The capsule 602 may include an agent such as a medicament and/or a fragrance or aromatic agent. As depicted in FIG. 6B, the arms 404a. 404b are configured to activate, pierce or burst the capsules 602 to release the agent, medicament and/or fragrance or aromatic agent when inserted into the sockets 408a, 408b. In this way, the medicament and/or fragrance or aromatic agent is released only when the capsule 602 is activated, pierced or burst, thereby increasing a longevity or "shelf-life" and/or protecting the integrity of the medicament and/or aromatic agent. For example, the agent may be an aromatic scent such as an essential oil blend or synthetic fragrance blend to provide an olfactory and/or physiological response such as decongesting the nasal passages 318, promoting relaxation, promoting sleepiness, suppressing appetite or a medicament such as a drug to reduce pain such as a migraine.

Figure 7A:
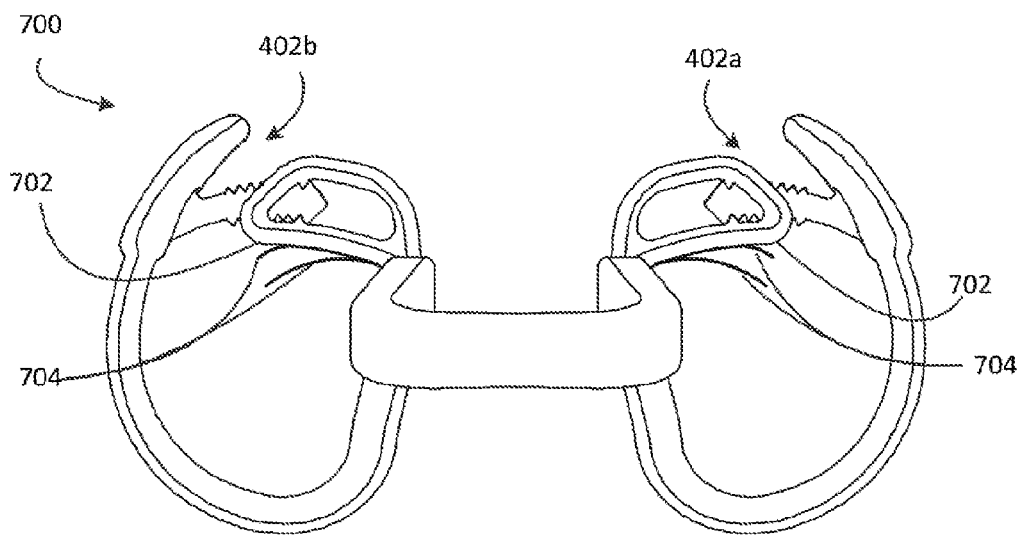
FIG. 7A is a front view of a nasal dilator device including a film according to some embodiments.
Figure 7B:
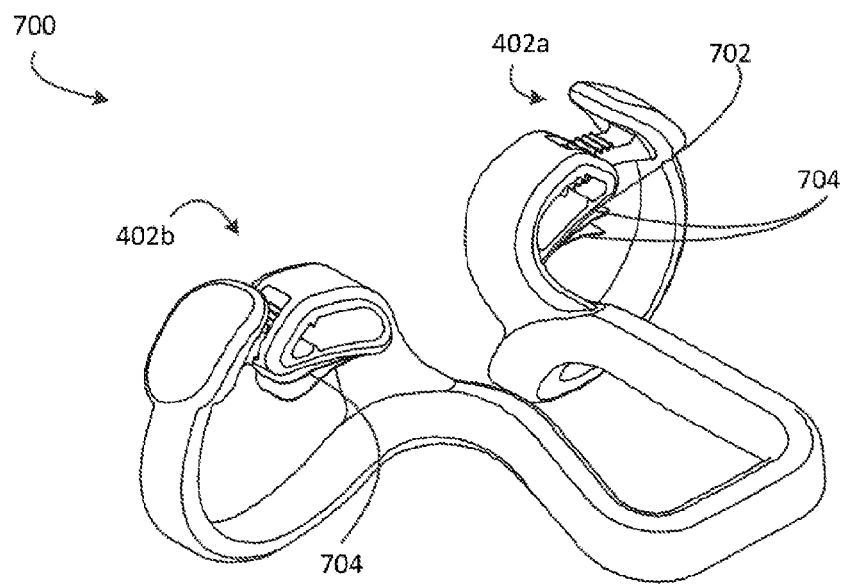
FIG. 7B is a front perspective view of the nasal dilator device of FIG. 7A.

Referring to FIGS. 7A and 7B, there is depicted the nasal dilator device 700 according to some embodiments. The nasal dilator device 700 may comprise similar components and elements to those of nasal dilator device 400 depicted in FIGS. 4A to 4D and accordingly those similar components and elements are denoted like numerals. The nasal dilator device 700 comprises at least one coating or film 702 arranged to release a fragrance, aroma or medicament. In some embodiments, the film 702 is arranged to release a fragrance, aroma or medicament in response to abrasion, such as scratching, scraping. The film 702 may be provided with an outer cover, seal or strip 704 to protect the film 702 from unintended abrasion, as depicted in FIGS. 7A and 7B at two separate stages of removal from the nasal dilator device 400.

In other embodiments, the coating or film 700 may be arranged to release a fragrance, aroma or medicament in response to the removal or peeling off of the outer cover, strip or seal 704. In some embodiments, a fragrance, aroma or medicament may be provided or retained between two strips or films 702 forming a blister.

The coating or film 702 may be comprise a polymer or a fibre. The coating or film 702 may be in the form of a "scratch and sniff" technology or peel off technology.

In some embodiments, as depicted in FIGS. 7A and 7B, the coating or film 702 may be disposed on a surface of at least one of the attachment mechanisms 402a, 402b, such as on an inner surface of the looped structures 411a, 411b. In other embodiments, the coating or film 702 may be disposed on the central portion 102, the first and second leg members 106a, 106b, the first and second intermediate sections 108a, 108b, the rib members 110a, 110b, and/or the first and second nostril engaging elements 112a, 112b.

In some embodiments, an aperture (not shown) is disposed in each of the first and second nostril engaging elements and is arranged to receive an agent, a compound, a medicament, a capsule, and/or a housing or compact arranged to receive an agent, medicament and/or a fragrance or aromatic agent. The agent may be absorbed by the inner walls of the nostrils transdermally and/or may be absorbed by mucosa in the nostrils 314.

Figure 8A:
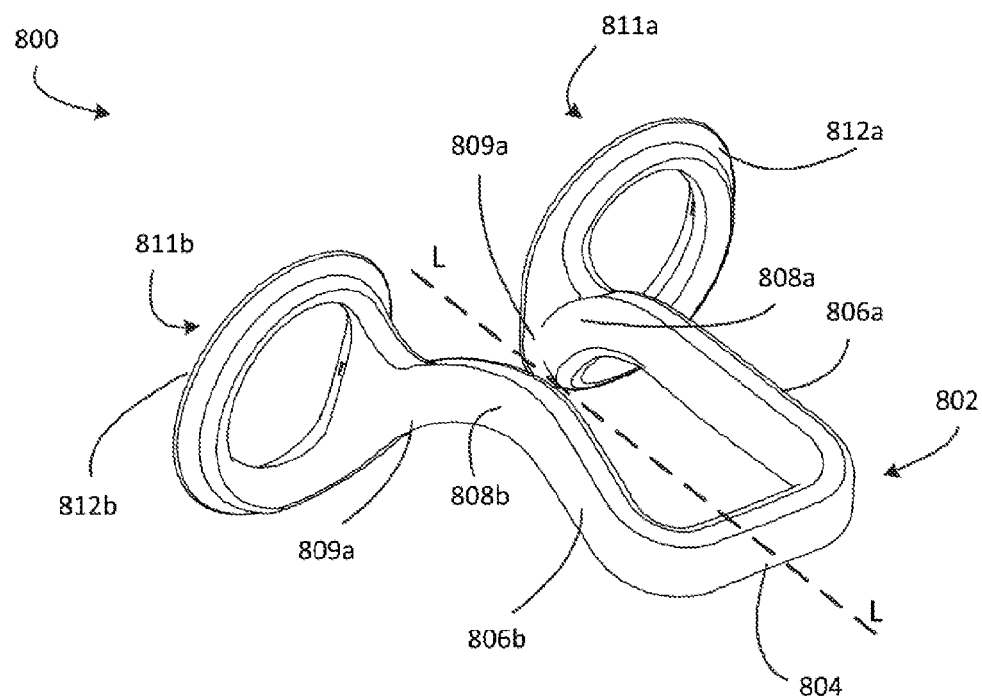
FIG. 8A is a front perspective view of a nasal dilator device according to some embodiments.
Figure 8B:
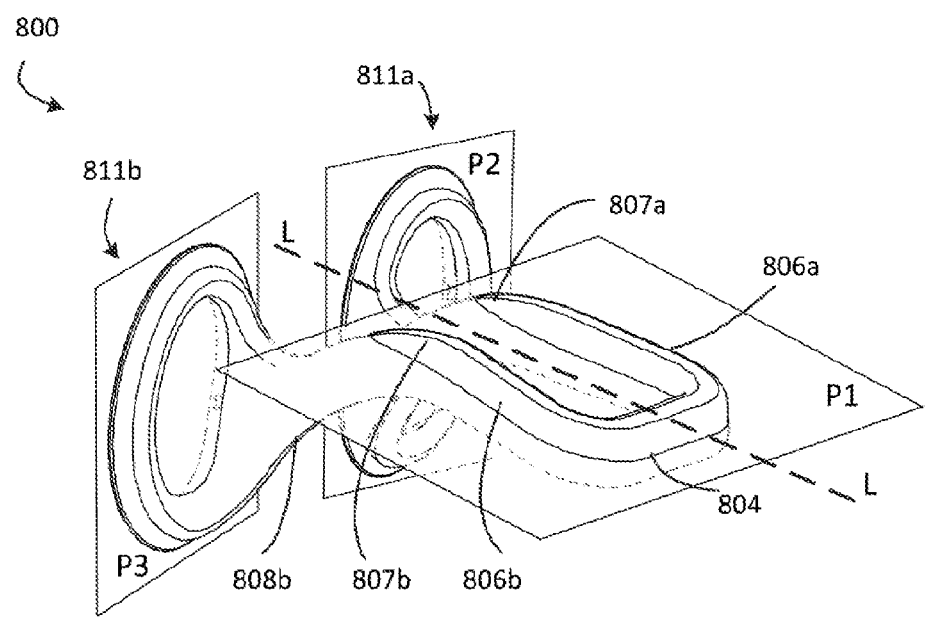
FIG. 8B is a further front perspective view of the nasal dilator device of FIG. 8A.

Referring to FIGS. 8A and 8B, there is depicted a nasal dilator device, generally indicated at 800 and substantially symmetrical about a longitudinal axis L, according to some embodiments. The nasal dilator device 800 may comprise a generally U-shaped body 802 having a central portion 804 and first and second leg members, 806a and 806b, respectively, extending from the central portion 804 in a first plane P1.

The nasal dilator device 800 comprises a first intermediate section 808a extending from an end 807a of the first leg member 806a and a second intermediate section 808b extending from an end 807b of the second leg member 806b. In some embodiments, and as depicted in FIGS. 8A and 8B, the first and second intermediate portions 808a, 808b, may be curved or arcuate along their length. In other embodiments, the first and second intermediate portions 808a, 808b may be substantially straight along their length or may comprise a plurality of angled or arcuate portions. For example, the first and second intermediate portions 808a. 808b may extend obtusely from the first and second ends 807a, 807b, for example, substantially at an angle of between approximately 95° and 130° to the longitudinal axis.

Figure 8C:
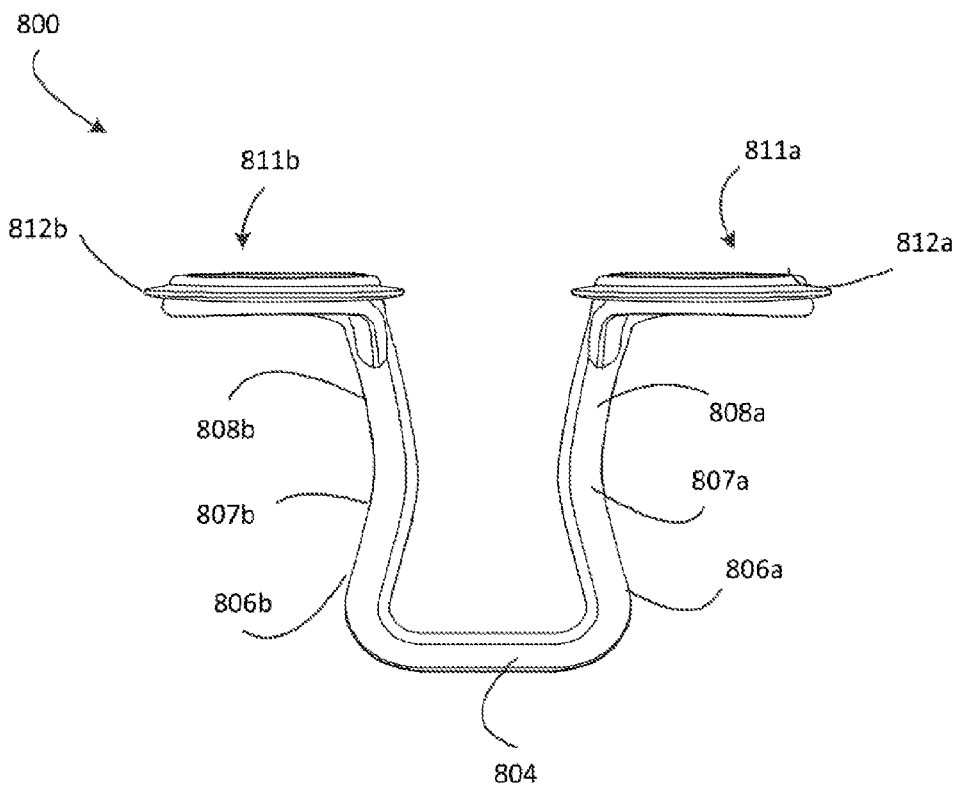
FIG. 8C is a top view of the nasal dilator device of FIG. 8A.

As depicted in FIGS. 8A to 8C, the nasal dilator device 800 comprises a first loop structure 811a projecting from the first intermediate section 808a in a second plane P2 and a second loop structure 811b projecting from the second intermediate section 808b in a third plane P3. In some embodiments, the first and second loop structures 811a, 811b may project substantially outward or lateral of the longitudinal axis of the generally U-shaped body 802 and away from one another. In some embodiments, the looped structure 811a, 811b may exhibit an elongate arched or curved profile which may substantially take the form of a circle, ellipse or parabola.

In some embodiments, the first intermediate section 808a may extend or transition between the first plane P1 and the second plane P2 to interconnect the end 807a of the first leg member 806a to a proximal end 809a of the first loop structure 811b and the second intermediate section 808b may extend or transition between the first plane P1 and the third plane P3 to interconnect the end 807b of the second leg member 806b to a proximal end 809b of the second loop structure 811b.

In some embodiments, the configuration of the first and second intermediate sections 808a, 808b may be associated with an orientation or location of the first and second loop structures 811a, 811b with respect to the U-shaped body 804. For example, the configuration of the first and second intermediate sections 808a, 808b may dictate or define an angle between the first and second planes, P1 and P2 and between the first and third planes, P1 and P3, respectively. The second and third planes, P2 and P3, may each form an acute angle, a right angle, or substantially right angle or an obtuse angle with the first plane P1. For example, the second and third planes P2 and P3, may be converging planes or intersecting planes and may each form an obtuse angle of approximately 95° to 130° with the first plane P1 such that the first and second intermediate sections 108a 108b take the form of obtuse arcuate sections. In some embodiments, the first, second and third planes, P1, P2, P3 may be different from each other and in some embodiments, the second and third planes, P2, P3 may be the same plane and may be different to the first plane P1.

In some embodiments, the first and second leg members 806a, 806b may be inclined toward each other or converge such that a relatively greater distance is provided between the first and second leg members 806a, 806b towards the central portion 804 in order to accommodate the columella 310 and to assist in holding the nasal dilator device 800 in place when worn.

In some embodiments, the first and second intermediate sections 808a, 808b may be inclined away from or diverge from one another to assist in urging the respective first and second loop structures 811a, 811b against inner walls of the nose when worn by the user.

In some embodiments, the first and second looped structures 811a and 811b may comprise first and second flanged portions, 812a and 812b, respectively. For example, the flanged portions 812a and 812b may provide additional compliance to the looped structures 811a, 811b. In some embodiments, the first and second flanged portions 812a and 812b may be comprise an overmould material, for example, flexible TPE, to thereby provide an improve sealing of the looped structures 811a and 811b to the nasal orifices.

Figure 9:
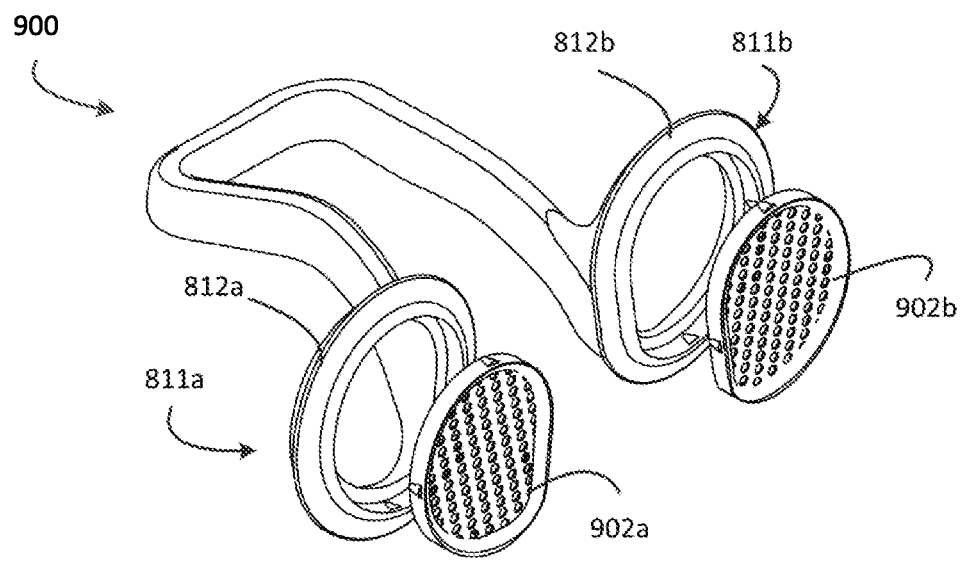
FIG. 9 is a rear perspective view of a nasal dilator device with an attachable filter, according to some embodiments.

Referring to FIG. 9, there is depicted the nasal dilator device 900 according to some embodiments. The nasal dilator device 900 may comprise similar components and elements to those of nasal dilator device 800 depicted in FIGS. 8A to 8C and accordingly those similar components and elements are denoted like numerals.

The first and second loop structures 811a, 811b, of the nasal dilator device 900 may be each arranged to receive a filter 902a, and 902b, respectively. The filters 902a, 902b, may be arranged or configured to span apertures defined by the first and second loop structures 811a, 811b.

The filters 902a, 902b may be composed of a fine woven mesh or an open celled porous material, such as a foam or compressed fibre. The filters 902a, 902b may be employed to filter out airborne particles such as bacteria, dust, pollens, and/or other allergens.

In some embodiments, as depicted in FIG. 9, the filters 902a, 902b, may be replaceable and may be arranged to be removeably connected to the first and second loop structures 811a, 811b respectively. For example, the filters 902a, 902b, may be configured to "snap-fit" into the first and second loop structures 811a, 811b respectively.

Figure 10:
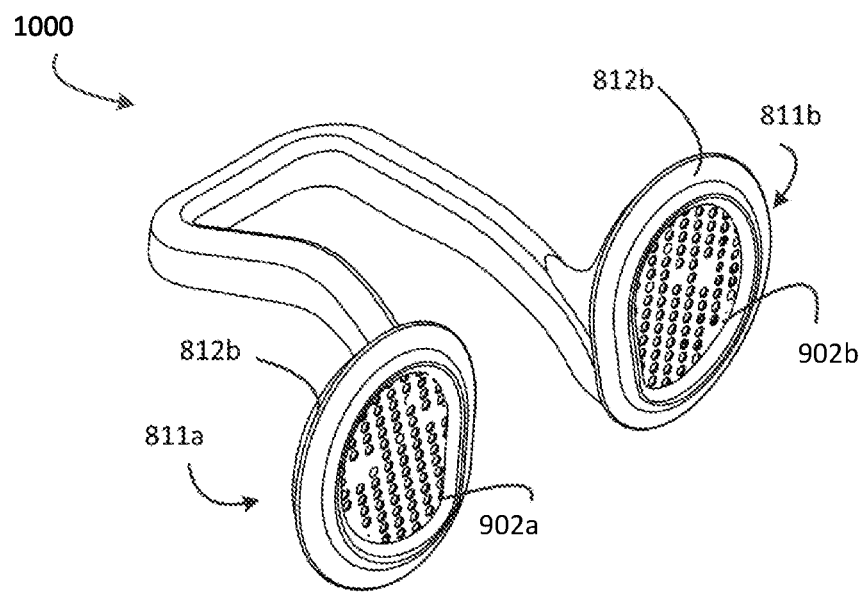
FIG. 10 is a rear perspective view of a nasal dilator device including a filter, according to some embodiments.

Referring to FIG. 10, there is depicted the nasal dilator device 1000 according to some embodiments. The nasal dilator device 1000 may comprise similar components and elements to those of nasal dilator device 800 depicted in FIGS. 8A to 8C and accordingly those similar components and elements are denoted like numerals The filters 902a, 902b of the nasal dilator device 1000 may be fixed to the first and second loop structures 811a, 811b respectively. For example, the filters 902a, 902b may be integrally formed with the first and second looped structures 811a, 811b or may be welded or ultrasonically welded to the first and second loop structures 811a, 811b.

In some embodiments, the nasal dilator device 100, 200, 400, 600, 700, 800, 900, 1000 may comprise an overmould disposed on at least one of the central portion, the leg members, the intermediate sections and the rib members. The overmould may be infused with a medicament and/or fragrance.

In some embodiments, the nasal dilator devices 100, 200, 400, 600, 700, 800, 900, 1000 may comprise a tab (not shown) extending outward from the central portion in a direction substantially opposite to the first and second leg members to assist with insertion, removal and/or placement of the nasal dilator device 100, 200, 400, 600, 700, 800, 900, 1000. The tab (not shown) may be removeable from the nasal dilator device, for example, by tearing the tab along a perforated line connecting the tab to the central portion 104, 804.

The U-shaped body 102, 802, the intermediate sections 108a, 108b, 808a, 808b, the rib members 110a. 110b, and the looped structure 811a, 811b may be composed of a polymer material such as thermoplastic elastomer (TPE) and/or thermoplastic polypropylene (PP). In some embodiments, the U-shaped body 102 and/or the intermediate sections 108a, 108b may are configured to be more rigid than the rib members 110a, 110b. For example, the U-shaped body 102 and/or the intermediate sections 108a, 108b and/or the rib members 110a. 110b may be composed of different materials or materials having differing hardness or stiffness. In some embodiments, the relative flexibility of the rib members 110a. 110b with respect to the U-shaped body 102 and/or the intermediate sections 108a, 108b may be derived from the length and/or thickness of the rib members 110a, 110b.

In some embodiments, an overall width of the nasal dilator device 100, 200, 400, 600, 700, 800, 900, 1000 may be in a range of approximately 20 mm to 35 mm when fully closed and approximately 25 mm to 40 mm when fully open, a length of the central portion 102, 802 may be in a range of approximately 5 mm to 10 mm, a length of the leg members 106a, 106b, 806a, 806b may be within a range of approximately 5 mm to 12 mm, and a length of the intermediate sections 108a, 108b, 808a, 808b may be in a range of approximately 7 mm to 15 mm and the rib members 110a, 110b, 810a, 810b may be in a range of approximately 15 mm to 30 mm. For example, in one embodiment, the overall width of the nasal dilator device 100, 200, 400, 600, 700, 800, 900, 1000 may be 25 mm when fully closed, 27.4 mm when open and the length of the leg members 106a, 106b, 806a, 806b may be 14.6 mm. In another embodiment, the overall width of the nasal dilator device 100, 200, 400, 600, 700, 800, 900, 1000 may be 27.2 mm when fully closed, 29.3 mm when open and the length of the leg members 106a, 106b, 806a, 806b may be 17.5 mm. In another embodiment, the overall width of the nasal dilator device 100, 200, 400, 600, 700, 800, 900, 1000 may be 29 mm when fully closed, 31.6 mm when open and the length of the leg members 106a, 106b, 806a, 806b may be 20.4 mm.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A nasal dilator device comprising:
   a substantially U-shaped body including:
      a central portion adapted to span a septum of a nose when worn by a user, and
      a first leg member and a second leg member extending from the central portion in a first plane;
   a first cantilever rib member extending outward from the U-shaped body in a second plane;
   a second cantilever rib member extending outward from the U-shaped body in a third plane;
   wherein the first cantilever rib member and the second cantilever rib member extend away from each other;
   a first intermediate section connecting an end of the first leg member to a proximal end of the first cantilever rib member, wherein a proximal end of the first intermediate section is connected to the end of the first leg member and a distal end of the first intermediate section is connected to the proximal end of the first cantilever rib member, wherein the first intermediate section extends between the first plane and the second plane such that, when said nasal device is in use and is worn by a user, the first intermediate section extends from the first leg member substantially downwards towards a floor of a respective nasal passage to the first cantilever rib member;
   a second intermediate section connecting an end of the second leg member to a proximal end of the second cantilever rib member, wherein a proximal end of the second intermediate section is connected to the end of the second leg member and a distal end of the second intermediate section is connected to the proximal end of the second cantilever rib member, wherein the second intermediate section extends between the first plane and the third plane such that, when said nasal device is in use and is worn by a user, the second intermediate section extends from the second leg member substantially downwards towards a floor of the respective nasal passage to the second cantilever rib member;
   a first and second releasable attachment mechanism for releasably attaching the first and second cantilever rib members, respectively, to the U-shaped body; and
   wherein the first leg member and the second leg member are inclined towards each other such that a greater distance is provided between the first leg member and the second leg member at ends of the first and second leg members closest the central portion relative to a distance provided between the first leg member and the second leg member at the ends of the first and second leg members connected to the first and second intermediate sections respectively, and
   wherein the first intermediate section and the second intermediate section are adapted, in use, to extend along a portion of the septum to the first cantilever rib member and the second cantilever rib member respectively, and
   wherein the first cantilever rib member and the second cantilever rib member are elongated and arcuate rib members, each having a curvature along its length, wherein the first cantilever rib member and the second cantilever rib member extend arcuately from the first intermediate section and the second intermediate section respectively in a substantially upward direction from the floor of the respective nasal passage to an inner wall of a respective nostril along their length in the second and third planes respectively when the nasal device is worn by a user.

2. The nasal dilator device of claim 1, wherein the first and second intermediate sections extend obtusely from the ends of the first and second leg members connected to the first and second intermediate sections respectively.

3. The nasal dilator device of claim 1, wherein the second and third planes are converging planes.

4. The nasal dilator device of claim 1, wherein the first and second cantilever rib members exhibit an elongated arched profile which approximates at least a portion of one of a circle, ellipse or parabola.

5. The nasal dilator device of claim 1, wherein the first and second intermediate sections are adapted to be inclined away from each other to assist in urging the respective first and second cantilever rib members against inner walls of respective nostrils when worn by the user.

6. The nasal dilator device of claim 1, wherein the first and second cantilever rib members comprise respective first and second nostril engaging elements comprising enlarged pads disposed thereon and adapted to engage with an inner wall of a respective nostril.

7. The nasal dilator device of claim 6, wherein the first and second nostril engaging elements are disposed at distal ends of the first and second cantilever rib members, respectively.

8. The nasal dilator device of claim 6, adapted to be orientated in the nose such that the first and second nostril engaging elements are adapted to be positioned at a junction of the greater alar cartilage and lateral nasal cartilage.

9. The nasal dilator device of claim 1, wherein the first and second releasable attachment mechanisms each comprise an arm and a socket arranged to receive and engage the arm.

10. The nasal dilator device of claim 9, wherein the releasable attachment mechanisms each comprise a stopper disposed at an end of the arm to hinder the arm from withdrawing from the socket.

11. The nasal dilator device of claim 9, wherein said arms are disposed on an inner surface of first and second nostril engaging elements of the first and second cantilever rib members, respectively, and said sockets are disposed on the first and second leg members or on the first and second intermediate sections.

12. The nasal dilator device of claim 1, wherein the first and second cantilever rib members comprise respective first and second nostril engaging elements for engaging with an inner wall of a respective nostril, wherein the first and second nostril engaging elements comprising enlarged pads disposed thereon, and wherein the first and second releasable attachment mechanisms are arranged to releasably attach the first and second nostril engaging elements to the first and second leg members respectively, or to the first and second intermediate sections respectively.

13. The nasal dilator device of claim 1, wherein the first and second releasable attachment mechanisms are adapted to allow a user to selectively adjust a degree of dilation or expansion and contraction of the first and second cantilever rib members with respect to the U-shaped body.

14. The nasal dilator device of claim 1, wherein in use the first and second intermediate sections are adapted to extend along a length of the septum behind the columella and the fibrofatty tissue or bulbous region around the base of the nostrils, and the first and second cantilever rib members are each adapted to extend from a floor of the nasal passage behind the columella and the fibrofatty tissue or bulbous region around the base of the nostrils to an inner wall of the nostrils.

15. The nasal dilator device of claim 1, wherein in use the first and second intermediate sections are adapted to cause the first and second cantilever rib members to use the floor of the nose as a support structure for dilation of the nostrils.

16. The nasal dilator device of claim 1, wherein in use the first and second cantilever rib members are each adapted to exert an outward force on the inner wall of the nostril and on the floor of the nose to thereby dilate the nasal passage of the nose.

17. The nasal dilator device of claim 1, wherein the first and second cantilever rib members are composed of a flexible material and are adapted to be squeezed or compressed by a user into a compressed state to allow insertion into the nasal passages of the nose and are biased to reform or revert to their uncompressed state once inserted into the nasal passage.

18. The nasal dilator device of claim 1, wherein:
(i) distal ends of the first and second cantilever rib member are not connected to the first and second intermediate sections respectively; and/or
(ii) the first and second intermediate sections each comprise a plurality of angled or arcuate portions along their length.

19. The nasal dilator device of claim 1, wherein the first and second cantilever rib members extend substantially upwardly along their length from the first and second intermediate sections respectively in a direction substantially toward the first plane.

20. The nasal dilator device of claim 1, wherein the first intermediate section extends substantially downward from the end of the first leg member to the proximal end of the first cantilever rib member, and the second intermediate section extends substantially downward from the end of the second leg member to the proximal end of the second cantilever rib member.

21. The nasal dilator device of claim 1, wherein when said nasal device is in use and is worn by a user:
the entire first intermediate section extends substantially downwards from the first leg member to the first cantilever rib member, and the entire second intermediate section extends substantially downwards from the second leg member to the second cantilever rib member; and/or
the entire first intermediate section transitions between the first plane and the second plane to interconnect the end of the first leg member to the proximal end of the first cantilever rib member, and the entire second intermediate section transitions between the first plane and the third plane to interconnect the end of the second leg member to the proximal end of the second cantilever rib member.

22. The nasal dilator device of claim 1, wherein each of the second and third planes forms an obtuse angle with the first plane such that the first and second intermediate sections are obtuse arcuate intermediate sections each having a substantially obtuse curvature along its length.

23. The nasal dilator device of claim 1, wherein each of the first cantilever rib member and the second cantilever rib member extends to a free distal end thereof.

24. A nasal dilator device comprising:
a substantially U-shaped body including:
a central portion adapted to span a septum of a nose when worn by a user, and
a first leg member and a second leg member extending from the central portion in a first plane;
a first cantilever rib member extending outward from the U-shaped body in a second plane;
a second cantilever rib member extending outward from the U-shaped body in a third plane;
wherein the first cantilever rib member and the second cantilever rib member extend away from each other;
a first intermediate section connecting an end of the first leg member to a proximal end of the first cantilever rib member, wherein a proximal end of the first intermediate section is connected to the end of the first leg member and a distal end of the first intermediate section is connected to the proximal end of the first cantilever rib member, wherein the first intermediate section extends between the first plane and the second plane such that, when said nasal device is in use and is worn by a user with a head of the user in a substantially upright position, the first intermediate section extends from the first leg member substantially downwards towards a floor of a respective nasal passage to the first cantilever rib member;
a second intermediate section connecting an end of the second leg member to a proximal end of the second cantilever rib member, wherein a proximal end of the second intermediate section is connected to the end of the second leg member and a distal end of the second intermediate section is connected to the proximal end of the second cantilever rib member, wherein the second intermediate section extends between the first plane and the third plane such that, when said nasal device is in use and is worn by a user with a head of the user in a substantially upright position, the second intermediate section extends from the second leg member substantially downwards towards a floor of the respective nasal passage to the second cantilever rib member; and
wherein the first leg member and the second leg member are inclined towards each other such that a greater distance is provided between the first leg member and the second leg member at ends of the first and second leg members closest the central portion relative to a distance provided between the first leg member and the second leg member at the ends of the first and second leg members connected to the first and second intermediate sections respectively, and wherein the first intermediate section and the second intermediate section are adapted, in use, to extend along a portion of the septum to the first cantilever rib member and the second cantilever rib member respectively, and wherein the first cantilever rib member and the second cantilever rib member are elongated and arcuate rib members, each having a curvature along its length, wherein the first cantilever rib member and the second cantilever rib member extend arcuately from the first intermediate section and the second intermediate section respectively in a substantially upward direction from the floor of the respective nasal passage to an inner wall of a respective nostril along their length in the second and third planes respectively when the nasal device is worn by a user.

25. A nasal dilator device comprising:
a substantially U-shaped body including
  a central portion arranged to span a septum of a nose when worn by a user, and
  a first leg member and a second leg member extending from the central portion;
a first cantilever rib member and a second cantilever rib member extending outward from the U-shaped body and away from one another;
a first intermediate section connecting an end of the first leg member to a proximal end of the first cantilever rib member, wherein a proximal end of the first intermediate section is connected to the end of the first leg member and a distal end of the first intermediate section is connected to the proximal end of the first cantilever rib member, wherein, when said nasal device is in use and is worn by a user, the first intermediate section extends from the first leg member substantially downwards towards a floor of a respective nasal passage to the first cantilever rib member; and
a second intermediate section connecting an end of the second leg member to a proximal end of the second cantilever rib member, wherein a proximal end of the second intermediate section is connected to the end of the second leg member and a distal end of the second intermediate section is connected to the proximal end of the second cantilever rib member, wherein, when said nasal device is in use and is worn by a user, the second intermediate section extends from the second leg member substantially downwards towards the floor of the respective nasal passage to the second cantilever rib member;
a first and second releasable attachment mechanism for releasably attaching the first and second cantilever rib members, respectively, to the U-shaped body;
wherein the first and second leg members are inclined towards each other such that a greater distance is provided between the first and second leg members at ends of the first and second leg members closest the central portion relative to a distance provided between the first and second leg members at the ends of the first and second leg members connected to the first and second intermediate sections respectively, and
wherein the first and second leg members are adapted, in use, to extend inward of respective nasal orifices along the septum;
wherein the first and second intermediate sections are arcuate and are adapted, in use, to extend along a portion of the septum to the first and second cantilever rib members respectively;
wherein the first and second cantilever rib members are elongated and arcuate rib members, each having a curvature along its full length, and wherein the first and second cantilever rib members extend arcuately from the first and second intermediate sections respectively in a substantially upward direction from the floor of the respective nasal passage to an inner wall of a respective nostril along their length when the nasal device is worn by a user.

* * * * *